(12) United States Patent
Shafer

(10) Patent No.: US 8,076,067 B2
(45) Date of Patent: Dec. 13, 2011

(54) PROBE-ANTIPROBE COMPOSITIONS AND METHODS FOR DNA OR RNA DETECTION

(75) Inventor: David A. Shafer, Atlanta, GA (US)

(73) Assignee: Genetag Technology, Inc., Atlanta, GA (US)

( * ) Notice: Subject to any disclaimer, the term of this patent is extended or adjusted under 35 U.S.C. 154(b) by 682 days.

(21) Appl. No.: 11/893,323

(22) Filed: Aug. 15, 2007

(65) Prior Publication Data

US 2009/0209434 A1 Aug. 20, 2009

Related U.S. Application Data

(60) Provisional application No. 60/837,788, filed on Aug. 15, 2006.

(51) Int. Cl.
*C12Q 1/68* (2006.01)
*C12P 19/34* (2006.01)
*C07H 21/00* (2006.01)
*C07H 21/02* (2006.01)
*C07H 21/04* (2006.01)

(52) U.S. Cl. ......... 435/6; 435/91.2; 536/22.1; 536/23.1; 536/24.3

(58) Field of Classification Search ............ 435/6, 91.2; 536/22.1, 23.1, 24.3
See application file for complete search history.

(56) References Cited

U.S. PATENT DOCUMENTS

| | | | |
|---|---|---|---|
| 4,965,188 A * | 10/1990 | Mullis et al. ............... 435/6 |
| 5,210,015 A * | 5/1993 | Gelfand et al. ............... 435/6 |
| 5,487,972 A * | 1/1996 | Gelfand et al. ............... 435/6 |
| 5,538,848 A * | 7/1996 | Livak et al. ............... 435/6 |
| 5,691,146 A * | 11/1997 | Mayrand ............... 435/6 |
| 5,723,294 A * | 3/1998 | Glass et al. ............... 435/6 |
| 5,723,591 A * | 3/1998 | Livak et al. ............... 536/22.1 |
| 5,866,336 A | 2/1999 | Nazarenko et al. ............... 435/6 |
| 5,925,517 A | 7/1999 | Tyagi et al. ............... 435/6 |
| 6,277,607 B1 | 8/2001 | Tyagi et al. ............... 435/91.2 |
| 6,326,145 B1 * | 12/2001 | Whitcombe et al. ............... 435/6 |
| 6,403,309 B1 * | 6/2002 | Iris et al. ............... 435/6 |
| 6,855,521 B2 * | 2/2005 | Callahan et al. ............... 435/91.2 |
| 2003/0219765 A1 | 11/2003 | Costa et al. ............... 435/6 |
| 2004/0259116 A1 * | 12/2004 | Beckman et al. ............... 435/6 |

(Continued)

FOREIGN PATENT DOCUMENTS

WO WO00/04192 * 1/2000
WO WO01/66802 * 9/2001

OTHER PUBLICATIONS

Chen et al. Fluorescence energy transfer detection as a homogeneous DNA diagnostic method. PNAS 94 : 10756-10761 (1997?). Cited by applicant.*

(Continued)

*Primary Examiner* — Ethan C Whisenant
(74) *Attorney, Agent, or Firm* — Thomas, Kayden, Horstemeyer & Risley, LLP

(57) ABSTRACT

The invention provides novel compositions and methods for detecting unlabeled nucleic acid targets using labeled polynucleotide probes and partially complementary antiprobes. The interaction of probes, antiprobes and targets result in signaling changes that indicate target frequency. This novel detection mechanism is called a DNA detection switch, and it enable end-point detection, microarray detection and real-time PCR detection of a variety of nucleic acid targets including microbial species and subspecies, drug resistant mutants, and pathogenic strains.

12 Claims, 14 Drawing Sheets

U.S. PATENT DOCUMENTS

2006/0292592 A1  12/2006  Happe et al. .................. 435/6
2009/0042735 A1*  2/2009  Blair et al. .................. 506/9

OTHER PUBLICATIONS

Didenko, V., DNA Probes Using Fluorescence Resonance Energy Transfer (FRET): Designs and Applications. Biotechniques 31 : 1106-1121 (Dec. 2001). Cited by applicant.*

Heller et al. Discovery and analysis of inflammatory disease-related genes using cDNA microarrays. PNAS 94 : 21502155 (1997).Cited by applicant.*

Matthews et al. Review : Analytical Strategies for the use of DNA probes. Analytical Biochemistry 169 : 1-25 (1988).*

Belanger et al., Rapid Detection of Shiga Toxin-Producing Bacteria in Feces by Multiplex PCR with Molecular Beacons on the Smart Cycler.J. Of Clinical Microbiology 40 (4) : 1436 (2002).*

Papin et al., SYBR Green-Based Real-Time Quantitative PCR Assay for Detection of West Nile Virus Circumvents False-Negative Results Due to Strain Variability. J. Of Clinical Microbiology 42(4) : 1511 (2004).*

Woo et al.,Identification of pathogenic Leptospira by TaqMan probe in a LightCycler. Analytical Biochemistry 280 : 132 (1998).*

* cited by examiner

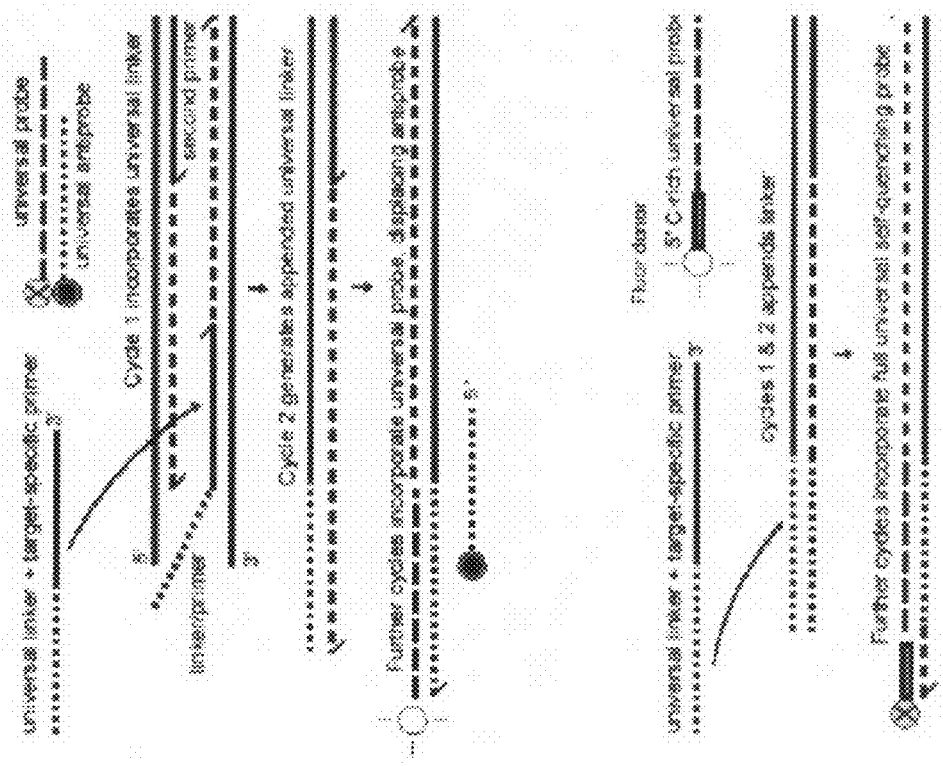
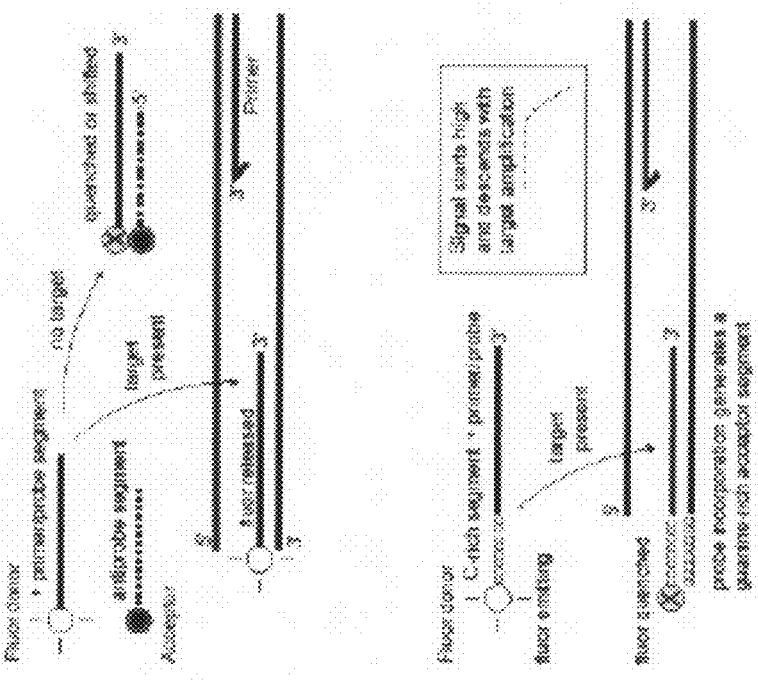
Fig. 4A
Fig. 4B
Fig. 3A
Fig. 3B

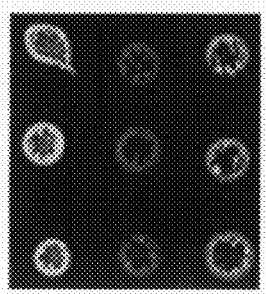
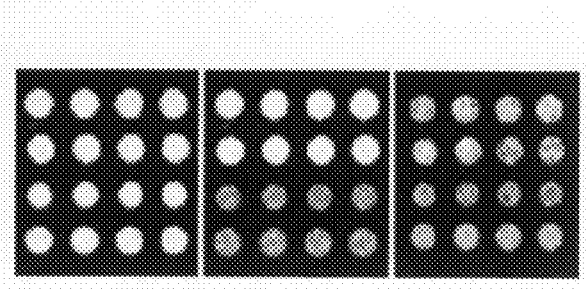
Fig. 7A             Fig. 7B
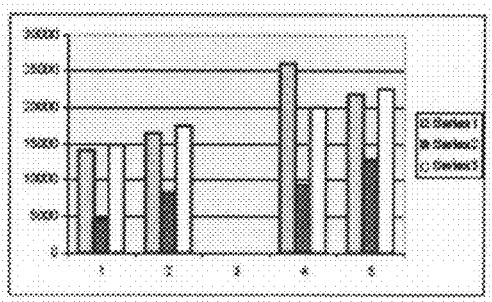
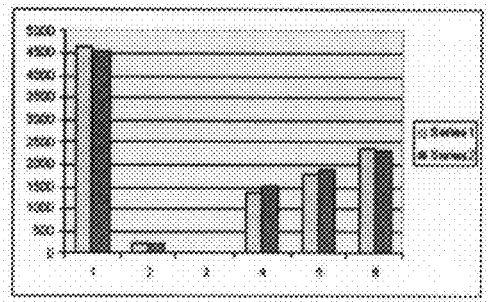
Fig. 8              Fig. 9
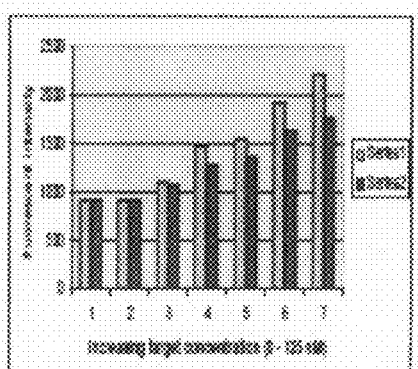
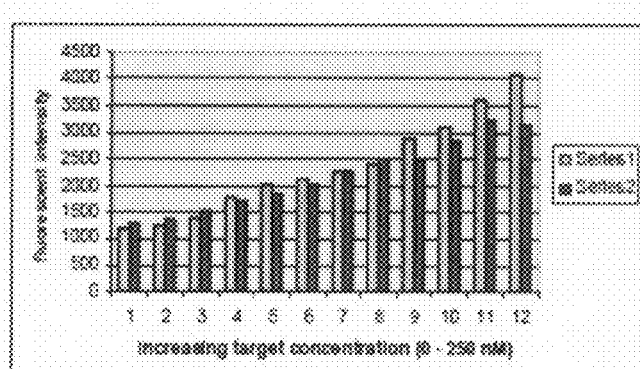
Type A/B  0-125 nM        Type A/B  0-250 nM
Fig. 10B            Fig. 10A

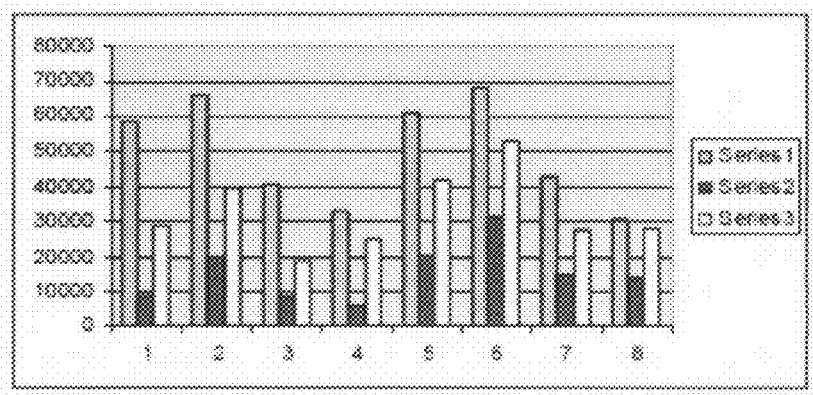
Fig. 11
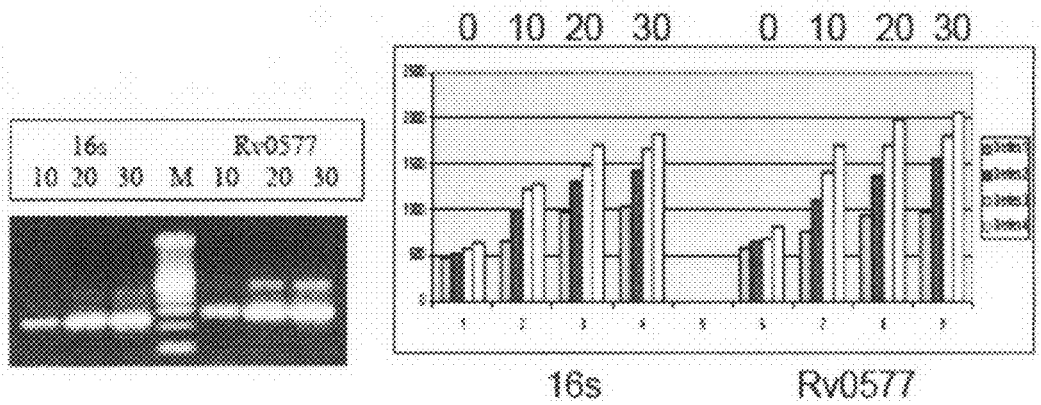
Fig. 12A
Fig. 12B
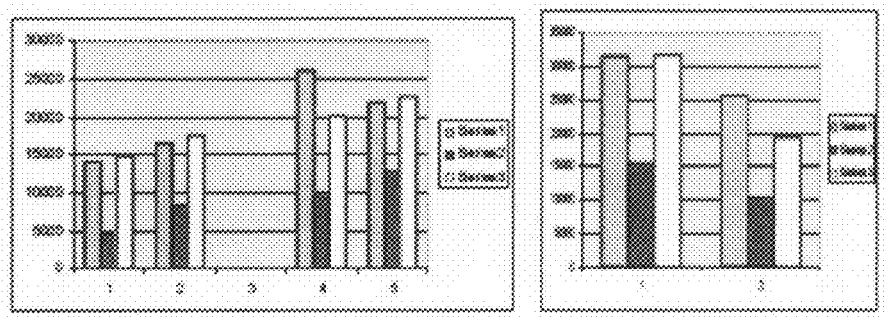
Fig. 13
Fig. 14

PROBE-ANTIPROBE COMPOSITIONS AND METHODS FOR DNA OR RNA DETECTION

CROSS-REFERENCE TO RELATED APPLICATION

This nonprovisional application claims benefit of priority of provisional U.S. Ser. No. 60/837,788, filed Aug. 15, 2006, now abandoned.

BACKGROUND OF THE INVENTION

1. Field of the Invention

This invention relates generally to the field of nucleic acid probe technology. More specifically, it relates to new compositions and methods to identify and quantify targeted DNA or RNA sequences, including single-base sequence variants in genomic and pathogenic samples. In particular it relates to new general probe systems to detect and assess target amplification by real-time PCR (polymerase chain reaction) with improved sensitivity, quantification and economy.

2. Description of the Related Art

The detection of targeted polynucleotide sequences is usually based on the use of short synthetic oligonucleotide probes or long cDNA based probes that are labeled and hybridized to a target sequence of interest. To work effectively, such probe products must be washed after hybridization to remove both unbound probes and probes that are weakly bound to non-specific targets. However, under the conditions of real-time PCR [U.S. Pat. No. 4,965,188; U.S. Pat. No. 5,210,015; U.S. Pat. No. 5,487,972; U.S. Pat. No. 5,538,848], a wash step is not feasible, and thus novel probes had to be devised that only generate signaling when they are bound to a complementary target and that have diminished or quenched signaling when they are unbound and floating free in solution.

To achieve this end, the prior art has generally relied on probes that employ FRET (fluorescent resonance energy transfer) interactions between a donor and an acceptor molecule, such as two fluorophores or a fluorophore and a quencher [Didenko V, Biotechniques, 2001, November; 31(5):1106-16, 1118, 1120-1121; Chen et al., Proc. Natl. Acad. Sci. USA, 1997, Sep. 30; 94: 10756-10762]. To work, the fluorescence emission spectrum of the donor must overlap the absorption or excitation spectrum of the acceptor.

In FRET, the excited-state energy of the fluorescent donor molecule is transferred to the acceptor molecule when they are brought into proximity (10 to 100 angstroms). If the acceptor molecule is fluorescent, signaling shifts to a longer wavelength. If the acceptor molecule is an effective quencher, fluorescent signaling is significantly diminished and may be essentially turned off. Taqman and Molecular Beacon probes are the principal FRET-based probes of this type for real-time PCR detection. In both cases, they serve as an internal probe that is used in conjunction with a pair of opposing primers that flank the target region of interest. When the primers amplify the target segment, the probe will selectively bind to those products at an identifying sequence in between the primer sites, thereby causing increases in FRET signaling relative to increases in target frequency. While these probe systems are therefore similar in effect, they employ somewhat different detection mechanisms.

More specifically, a Taqman probe comprises a synthetic oligonucleotide of about 22 to 30 bases that is complementary to a target sequence and that is labeled on both ends with a FRET pair [Livak et al. 1996, U.S. Pat. No. 5,538,848]. Typically, the 5' end will have a shorter wavelength fluorophore such as fluorescein (e.g. FAM™) and the 3' end is commonly labeled with a longer wavelength fluorescent quencher (e.g. TAMRA™) or a non-fluorescent quencher compound (e.g. Black Hole Quencher™). In solution, the probe will randomly coil or fold so that the labeled ends are in proximity and 5' fluorescent emissions are effectively quenched. But when the probe binds to an internal target sequence during the annealing step of PCR, the advancing Taq polymerase has 5'-3' exonuclease activity that will degrade the bound probe, permanently releasing the components in solution. Once a 5' fluorophore is thereby released, it can emit fluorescent signaling, and thus the level of fluorescence that results is proportional to the frequency of amplified targets.

Taqman probes evolved from an earlier system based on 5'-3' exonuclease digestion using internal probes with simply a 5' fluorescent end. When the probe was digested via polymerase advance, the released fluorescent fragments were thereafter detected [U.S. Pat. No. 5,210,015; U.S. Pat. No. 5,487,972]. One common requirement for designing such fluorescent probes is that there be no guanine (G) at the 5' end since a G adjacent to the reporter dye will significantly quench reporter fluorescence even after the probe is degraded.

Like TaqMan probes, Molecular Beacon probes use FRET interactions to detect and quantify a PCR product, with each probe having a 5' fluorescent-labeled end and a 3' quencher-labeled end. [Tyagi et al. 1999, U.S. Pat. No. 5,925,517; Tyagi et al., Nature Biotechnology 1996, 14: 303-8]. However, Molecular Beacons also include short artificial segments of 5 to 7 bases at each end that are complementary to one another but not complementary to the target. In the absence of target binding, these matching end sequences will bind together in solution, thereby bringing the quencher-labeled end in proximity to the fluorophore-labeled end so that fluorescent signaling is suppressed.

This probe structure has been described as a hairpin or stem-loop configuration, wherein the stem depicts the two short self-binding ends and the loop depicts the long internal target-specific region of about 20 to 30 bases. Due to this configuration and the relatively greater length of the target-specific region, these probes will preferentially hybridize to available complementary targets, thereby causing the probes to straighten and extend since double-stranded DNA is relatively rigid like a spring as compared to single-stranded DNA which is floppy and easily folded like a string. Consequently, with target binding, the labeled ends of the probe will separate from one another, thereby releasing fluorescent emissions. Because this mechanism does not depend on degradation of the probe, Molecular beacons can be employed in a variety of detection schemes in addition to real-time PCR assays. A similar detection mechanism is employed by an independent invention wherein the probe is fabricated with only the loop structure and without the short complementary stem regions [Mayrand et al. 1997, U.S. Pat. No. 5,691,146]. This method also works because in the absence of target binding the fluor-labeled and quencher-labeled ends will naturally fold or coil together to significantly quench fluorescence, whereas, when target binding occurs, these probes will automatically stretch out, thereby releasing fluorescence.

An alternative FRET-based approach for PCR and real-time PCR detection uses two hybridization probes that bind to adjacent sites on the target wherein the first probe has a fluorescent donor label at the 3' end and the second probe has a fluorescent acceptor label at its 5' end [Wittmer et al. Biotechniques, 1997, 22: 130-138]. When both probes bind to the template, bringing the donor and acceptor labels into proximity, the FRET interaction occurs causing a color shift in fluorescent signaling. Thus PCR amplification causes an exponential increase in the ratio of acceptor fluorescence versus donor fluorescence which is proportional to the amount of target DNA generated.

Scorpion™ probes provide a FRET-based stem-loop detection mechanism similar to Molecular Beacons, except that the probe also has a segment attached that serves as an amplification primer [Whitcombe et al. Nat Biotechnol. 1999, Aug. 17(8): 804-7; U.S. Pat. No. 6,326,145]. Like Molecular Beacons, these probes maintain a stem-loop configuration in the unhybridized state with the fluorophore thereby quenched. However, they have a longer multi-component structure. First there is a 5' fluorophore, then a target-specific stem-loop section, then a Black Hole Quencher™, then a hexethylene glycol (HEG) blocker and finally a 3' primer sequence. The blocker prevents reverse extension of the product onto the probe. After primer extension occurs, the Scorpion probe is attached to the terminal end of the amplicon. When denaturation occurs again, followed by annealing, the loop segment of the probe will preferentially bind to its long complementary segment on the attached template, thereby opening the stem-loop structure and releasing fluorescence.

Alternatively, the stem-loop structure is cut into two units with one unit having four components, i.e., the 5' fluorophore, the target specific segment, the blocker and the primer, and with the other unit having the quencher and a probe segment. Similar to Scorpion probes, Sunrise™ probes comprise a primer attached to a hairpin probe that is extended during amplification. This separates the internal quencher label from the 5' terminal fluorophore [Nazarenko et al., Nucl. Acids Res. 1997, 25: 2516-2521].

All these dual-labeled FRET-based probes require careful design and they are quite expensive. Their synthesis is difficult and they require manual post-synthesis addition of at least one label as well as high pressure liquid chromatography to purify for double-labeled products. Taqman and Molecular Beacon probes also require the design of two opposing primers that must work in conjunction with the probe. In order to function effectively during the annealing step, Taqman and Molecular Beacon probes must be longer and have a Tm that is 5 to 10 degrees higher than the primers since the probe must bind firmly to the target before extension. For Taqman probes this condition is needed to digest and release fluorescence. For Molecular Beacons, this condition is similarly essential to stretch out and release fluorescence. However, at the same time, the requirement for a long target-specific probe makes it much more difficult to design and develop probes that can selectively detect small sequence changes such as SNPs (single nucleotide polymorphisms) or single base mutations. Therefore, these hybridization-based probes generally require multiple designs and repeated testing in order to achieve a working or optimal result.

In other detection formats, different issues are important. When gene targets are detected by FISH (fluorescent in situ hybridization) four processing steps are typically required: 1) the preparation of labeled probes, 2) probe hybridization to fixed denatured targets, 3) the washing of unbound probes, and 4) fluorescent excitation and detection [Barch M J, editor. The ACT Cytogenetics Laboratory Manual. 2nd ed. New York: Raven Press; 1991]. Careful wash steps are critical to effective detection since the signal to noise ratio is highly dependent on the stringency of washing and since excessive washing can greatly reduce signaling. Thus FISH probes generally require a delicate, graded series of critically timed wash steps, using different components and dilutions, all of which add considerably to the time, complexity and cost of such assays.

Microarray detection is somewhat similar to FISH detection. Arrays are typically based on printing glass or silicon substrates with bound oligo probes or cDNA probes; applying fluorescent-labeled DNA or RNA targets which must be hybridized to the probes; washing the arrays stringently; and then detecting the bound targets—usually by laser scanning [Schena et al. 1995, Science 270: 467-470; Heller et al. 1997, P.N.A.S. USA, 94, 2150-2155]. Like FISH probes, the wash steps are again complex and time consuming. However, the preparation and labeling of the targets are an expensive additional process since each target sample is unique. Indeed, the cost and time burden of current target labeling and detection methods is the major limitation to the routine use of microarray-based assays.

The present invention significantly overcomes many of the limitations described above and provides advantages over the prior art for microarray detection, FISH detection and PCR detection. In addition, several embodiments of the present invention enable more definitive quantification of real-time PCR products, whereas such assays typically require running concurrent standards and controls in order to certify results.

The invention is especially directed towards the detection of single base variants important to discriminating bacterial and viral pathogens, including drug resistant mutants. Of particular interest, HIV-1 resistance-related targets have defied detection with ordinary real-time PCR probe systems or with hybridization-based microarray probes because these critical single base mutations commonly occur in a sea of nearby unrelated mutations [Shafer, R. W. 2002, Clin Microbiol Rev 15: 247-277; D'Aquila et al. 2002, Topics HIV Med 10: 21-25; Gonzalez et al. 2004, Journal of Clinical Microbiology, 42 (7): 2907-2912; Gunthard et al. 1998, AIDS Res Hum Retroviruses 14: 869-876]. Overcoming these difficult detection limitations has been a goal as well as an accomplishment of the present invention.

There is a recognized need in the art for improved detection of nucleic acid targets. Specifically, the prior art is deficient in the lack of a simple method for detecting single or multiple polynucleotide target sequences by employing novel probe and antiprobe compositions and detection strategies in various liquid and solid phase detection platforms. The present invention fulfils this longstanding need in the art.

SUMMARY OF THE INVENTION

The present invention is directed to a probe-antiprobe composition. The composition comprises a polynucleotide probe comprising a sequence complementary to a target sequence and a polynucleotide antiprobe comprising a sequence complementary to a partial segment of the probe either substantially within or outside of the target complementary sequence of the probe, wherein the probe and antiprobe further comprise a pair of interacting labeling components such that the binding of probe and antiprobe comprises a first signaling state and the binding of probe and target comprises a second signaling state. This general composition called a DNA detection switch (DDS) is effective to detect the target nucleic acid in a sample. Various embodiments of this invention are presented that enable end point detection, microarray detection and real-time PCR amplification and detection.

The present invention is also directed to a universal probe-antiprobe composition. The composition comprises: a universal probe having 3' primer sequence that substantially corresponds to a 5' universal linker sequence of a linker/primer, which itself further comprises a 3' target-specific primer sequence, and where the universal linker sequence does not match or complement a sequence in the target sample and a universal antiprobe complementary to a partial sequence segment of the universal probe, wherein the probe and antiprobe are labeled with a pair of interacting labeling components that comprise a first signaling state when they are bound together and a second signaling state when the probe is bound to a target. The composition is effective to amplify and detect one or more amplified target sequences in a sample.

The present invention is also directed to a self-quenching probe-antiprobe composition. The composition comprises two components hybridized together: (i) a synthetically-fabricated polynucleotide primer/probe component having a 5' label, a 3' primer sequence segment complementary to a target sequence, and an artificial cytidine-rich sequence comprising one or more cytidine bases that is inserted adjacent to the label, and (ii) an enzymatically-generated antiprobe component comprising an amplified DNA segment that comprises both a natural target sequence complementary to the 3' primer sequence of the probe and an artificial guanine-rich sequence complementary to the artificial cytidine-rich sequence of the probe, wherein said two component composition is generated by priming and amplifying a segment of the natural target sequence with the self-quenching primer/probe described supra; and wherein the presence and frequency of said amplified targets is detected by a change in probe signaling.

The present invention is also directed to a refined probe-antiprobe composition for detecting and discriminating small sequence differences of interest between closely related target sequences such as SNPs or single base mutations. The composition comprises a first component, a polynucleotide probe having a sequence segment complementary to the intended target sequence, and a second component, a polynucleotide antiprobe that comprises a sequence complementary to a partial sequence of the probe; wherein the probe and antiprobe are labeled with a pair of interacting labels; wherein the antiprobe is designed to locate the small targeted sequence difference of interest within the central two-thirds of the antiprobe sequence; and the position, length and sequence composition of the antiprobe relative to the probe is further selected so that (i) the Tm between the probe and the intended target sequence is higher than the Tm between the probe and the antiprobe, and so that (ii) the Tm between the probe and the antiprobe is higher than the Tm between the probe and an incorrect mismatched target sequence. The composition is effective in creating a dynamic equilibrium in solution that favors the binding of the probe to a correct matching target, and that favors the binding of the antiprobe to the probe in the face of an incorrect mismatched target, thereby detecting a correct target and avoiding or preventing the detection of a closely-related, mismatched target.

The present invention is also directed to a probe-antiprobe composition for real-time PCR detection wherein the probe binds to an internal target sequence between two flanking primers. The composition comprises a probe and antiprobe as described supra that is labeled on one or both ends of the probe and antiprobe, and that is chemically modified on any unlabeled 3' end to prevent polymerase extension; wherein the length and sequence of the antiprobe is designed to comprise a Tm that is substantially equivalent to the Tm of the primers and that is substantially lower than the Tm of the probe; wherein the binding of probe and antiprobe brings the labeling components together and comprises a first signaling state; and wherein the binding of probe and target separates the labeling components and comprises a second signaling state, wherein amplification is monitored by detecting the changes in signaling state that occur each PCR cycle.

The present invention is directed further to a method of real-time amplification and detection of an amplified target using first and second stage priming, comprising, (a) providing, for the first-stage priming, the universal linker/primer described supra; (b) providing, for the second-stage priming, the universal primer/probe and antiprobe described supra or the universal self-quenching primer/probe described supra; (c) amplifying the target product by primer extension, wherein the first and second stage primer components are provided simultaneously or sequentially; and (d) monitoring label signaling which is modulated relative to target frequency.

The present invention is directed further yet to a method for multiplex amplification and simultaneous detection of a plurality of polynucleotide target segments. The method comprises providing primer and probe sets to detect each target where each set may be (i) a standard primer/probe and antiprobe, or (ii) a self-quenching primer/probe, or (iii) a universal linker/primer, a universal primer/probe, and a universal antiprobe, or (iv) a universal linker/primer and a self-quenching universal primer/probe, or (v) a primer set and an internal probe and antiprobe set; wherein each probe set has either a different label color to identify each target product separately or the same label color to combine detection of all products together; and amplifying the targets by selective primer extension, wherein separate or combined target product frequency is monitored by detecting the changes that occur in label signaling.

Other and further aspects, benefits and advantages of the present invention will be apparent from the following description of the presently preferred embodiments given for the purpose of disclosure.

BRIEF DESCRIPTION OF THE DRAWINGS

The appended drawings have been included herein so that the above-recited features, advantages and objects of the DDS probe-antiprobe invention will become clear and can be understood in detail. These drawings form a part of the specification. It is to be noted, however, that the appended drawings illustrate preferred embodiments of the invention and should not be considered to limit the scope of the invention.

FIG. 2A shows the use of one segment probes with target specific antiprobes. FIG. 2B shows the use of two segment probes with a generic antiprobe that binds to a tail segment of the probe at some distance from the fluorescent-labeled end. In both cases, target binding to the probe will release fluorescence that is otherwise quenched or shifted via antiprobe binding. See examples 2-8.

FIGS. 3A-3B depict an extension of the basic probe-antiprobe mechanism described above to real-time PCR detection. FIG. 3A shows the use of a fluorescent donor-labeled probe that also serves as a primer for PCR amplification, and that works in conjunction with a long partially-complementary antiprobe with fluorescent acceptor or quencher labeling that turns off the signaling of free floating primer/probes when they are not incorporated into an amplified target. Thus primer/probe signaling goes up as amplicons are generated, providing real-time detection curves that profile the time course of exponential target amplification. FIG. 3B shows the mechanism of a self-quenching primer/probe in which a string of cytidine bases are inserted between the fluorescent label and the primer sequence to generate an artificial string of guanine bases in newly formed complementary strands that quench primer/probe fluorescence as target products are made. With this self-quenching primer/probe mechanism, signaling starts high and goes down as amplification proceeds. See examples 9-16.

FIGS. 4A-4B depict universal primer/probe methods for real-time PCR detection wherein product amplification proceeds in two stages during thermal cycling. In FIG. 4A, in the first stage, one target-specific primer carries a universal linker sequence appended to its 5' end that generates initial products with a universal primer site and then a universal primer/probe, in conjunction with a universal antiprobe, takes over further target amplification and provides real-time detection. FIG. 4B shows that same process, but uses a self-quenching universal primer/probe that carries a string of c bases inserted between the fluorescent label and the universal primer sequence. Both mechanisms enable the use of a generic universal probe for real-time detection of any target sequence of interest. See example 17.

FIGS. 7A-7B demonstrate that signaling is detectable in an array. FIG. 7A depicts a hand-spotted array on a coated slide in which various mixes of probes, antiprobes and targets were applied and detected with a microarray scanner. FIG. 7B depicts a segment of a machine-spotted array at three time points showing that the signaling of a specific probe (the lower 8 dots of each panel) is diminished by quencher addition (mid-panel) and restored by target addition (right panel). See Example 1.

FIG. 8 depicts end-point detection of a M tuberculosis target with the primary probe-antiprobe methods using a fluorescent plate reader. The same probes are combined with different antiprobes (target-specific and generic) to show both type A and B detection. (bars: gray=probe, dark gray=probe+quencher, light=probe+quencher+target) see Example 2.

FIG. 9 depicts type a and b end-point detection of a human rab9 gene segment and comparing different concentrations of the target. See Example 3.

FIGS. 10A-10B depict further tests of type A and B end-point detection with target concentrations ranging from 0 to 125 nm (FIG. 10A) and 0 to 250 nm (FIG. 10B). See Example 4.

FIG. 11 depicts tests of type a and b end-point detection with different lengths of the target specific segments of the probe. (type A=sites 1-4, type B=sites 5-8) see Example 5.

FIGS. 12A-12B depict quantitative detection of unlabeled raw PCR products by end-point detection with probe-antiprobe methods. FIG. 12A shows a gel of the two test products at 10, 20 and 30 cycles of PCR. FIG. 12B shows a graph of progressive signaling with a series of 5 ul aliquots of raw product added to the probe-antiprobe mix. See Example 6.

FIG. 13 depicts end point detection with reverse-labeled type A and B probes and antiprobes. See Example 7.

FIG. 14 depicts end-point detection of PCR products (site 1) versus oligo targets (site 2) with reverse-labeled DDS probes. See example 8.

FIG. 19A shows 96% wild vs. 99.5% wild. FIG. 19B shows the remaining 4% mutant vs. 0.5% mutant from the same two samples as FIG. 19A. Thus, low frequency mutants can be quantified. See Example 13.

DETAILED DESCRIPTION OF THE INVENTION

Figure 1A:
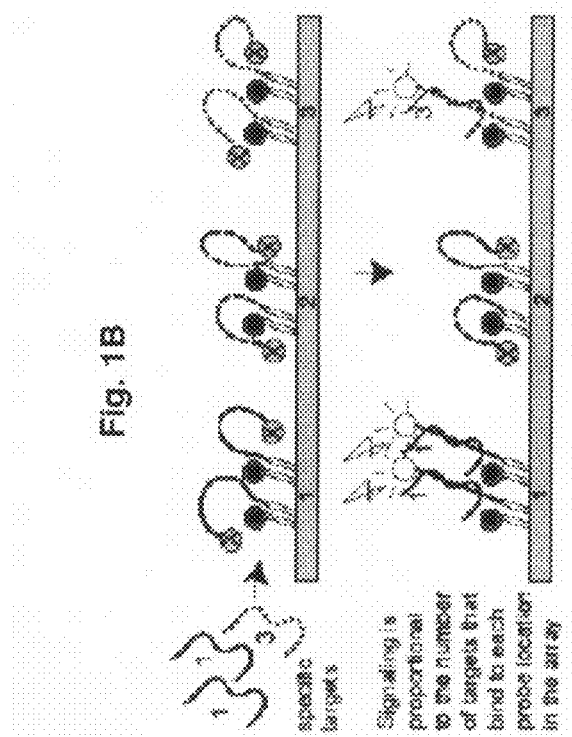
FIGS. 1A-1B depict two array-based probe and antiprobe compositions where the probes are attached to a substrate and floating antiprobes and targets bind to the probes to give signaling relative to target frequency. The type A composition employs a one segment probe and a short antiprobe that binds to a target-specific sequence of the probe adjacent to the labeled end. The type B composition employs a two segment probe wherein the target binds to the segment adjacent to the labeled end of the probe, and the short antiprobe binds to a second segment at a distance from the labeled end of the probe (FIG. 1A). The type B composition enables the use of a generic antiprobe that serves to modulate the fluorescent signaling of all probes in an array (FIG. 1B). In both compositions, unlabeled targets provide a signaling change when they are bound to specific probes in the array. See details in example 1.
Figure 1B:
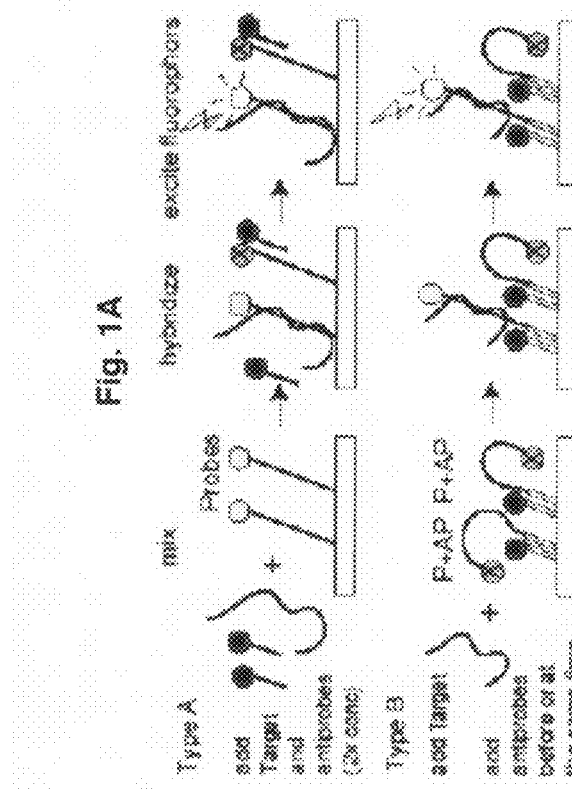
Figure 2A:
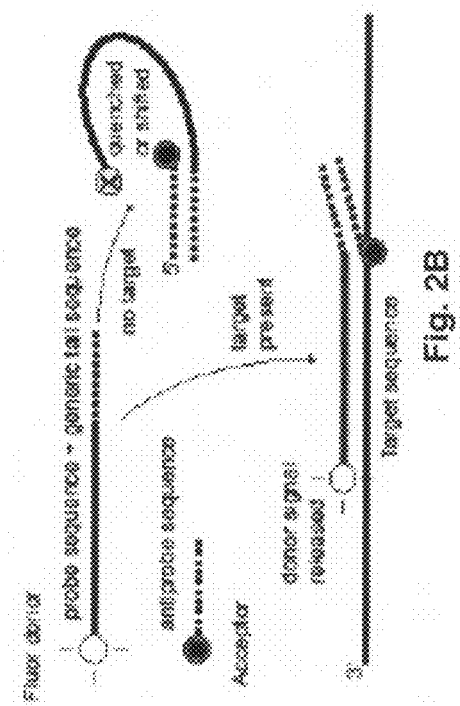
FIGS. 2A-2B depict the design and application of the same two primary probe-antiprobe mechanisms to achieve end point detection of DNA or RNA targets in solution.
Figure 2B:
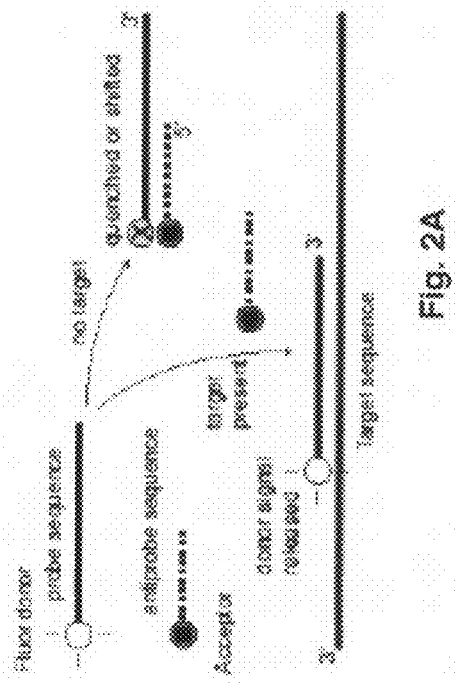
Figure 5:
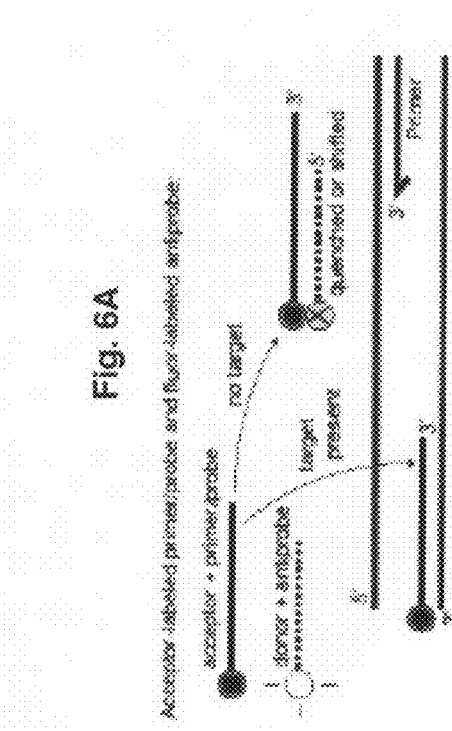
FIG. 5 depicts probe-antiprobe detection wherein a pair of ordinary opposing primers are employed and wherein the probe component binds to an internal sequence of the target amplicon in the same manner as Taqman or Molecular Beacon probes. For this modification, the 3' end of the probe is typically blocked to prevent it from extending. This mechanism works with probes and antiprobes that are significantly shorter than traditional Taqman probes and thus they provide greater specificity. See example 14.
Figure 6A:
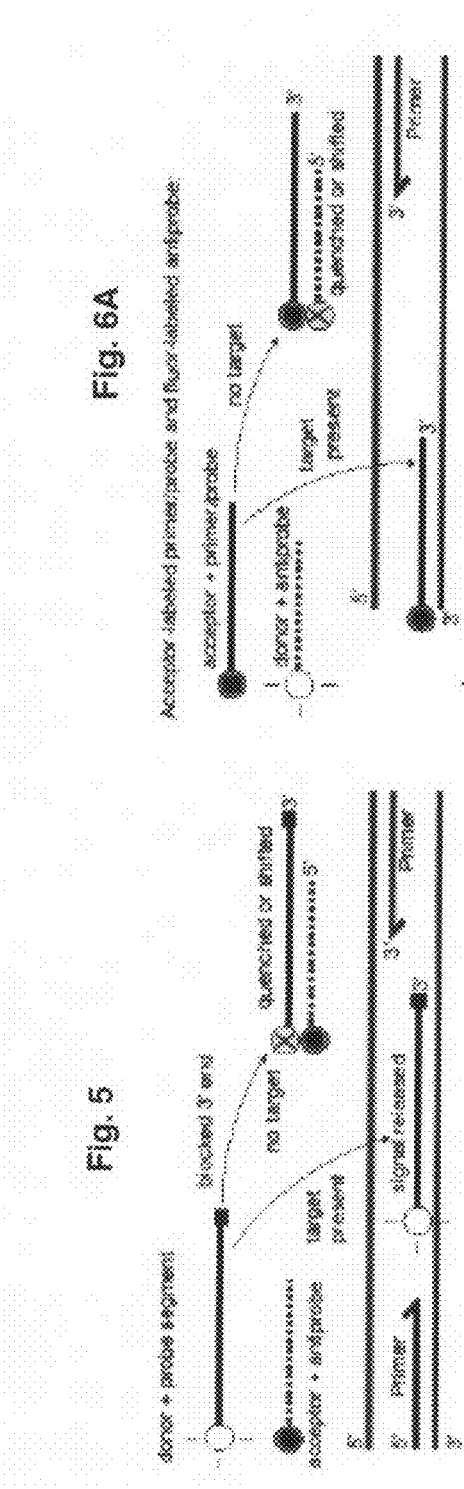
FIG. 6A depicts reverse-labeled primer/probes and antiprobes wherein the primer/probe is 5' labeled with an acceptor moiety and the antiprobe is 3' fluorescent donor-labeled. Primer/probe incorporation in the product displaces or releases the fluor-labeled antiprobes so that signaling increases with amplification. See example 18.
Figure 6B:
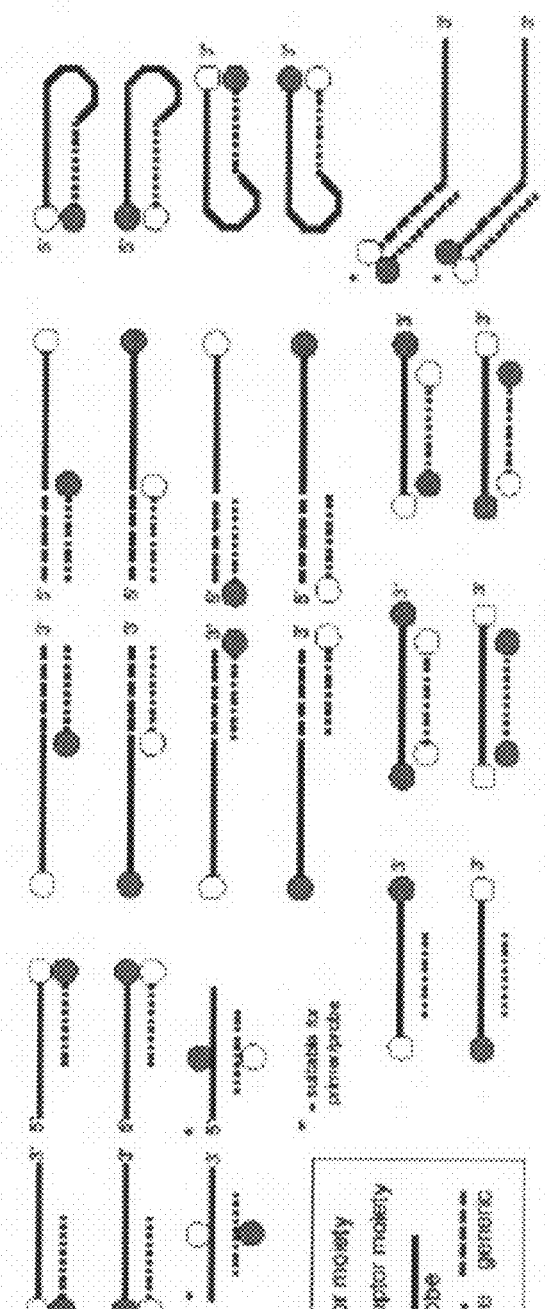
FIG. 6B depicts various examples of alternate labeling configurations for DDS probe antiprobe compositions. The configurations suitable for DDS primer/probe use are marked with a star. Most variations are suitable for an internal DDS probe for a target sequence between flanking primers. In such applications, any unlabeled 3' ends must be blocked to prevent extension. Many of these variations have been tested with a fluorescent donor label paired with an acceptor moiety that comprises either a quencher compound, a longer wavelength fluorescent compound or a guanine rich segment appended to the probe which serves as a quencher. Detection sensitivity depends on the labeling pairs utilized.

As used herein, the term "a" or "an", when used in conjunction with the term "comprising" in the claims and/or the specification, may refer to "one", but it is also consistent with the meaning of "one or more", "at least one", and "one or more than one". Some embodiments of the invention may consist of or consist essentially of one or more elements, method steps, and/or methods of the invention. It is contemplated that any device or method described herein can be implemented with respect to any other device or method described herein.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof.

As used herein, the term "probe" shall refer to a polynucleotide containing a sequence complementary to a target and further comprising a signaling component such as a label, or alternatively, a label modulator.

As used herein, the term "label" shall refer to any component or reagent that provides or modifies a detectable signal, such as a fluorescent compound.

As used herein, the term "label modulator" shall refer to any component or reagent that modifies the signaling of a label, such as a quencher compound, another fluorescent compound or other signal modulating components.

As used herein, the term "antiprobe" shall refer to a polynucleotide that interacts with a probe by virtue of a partial complementary sequence and a signaling component, such as a label modulator or a label. An antiprobe is a new term that defines novel compositions of to the present invention.

As used herein, the term "target-specific antiprobe" shall refer to an antiprobe comprising a sequence that is both in common with a target sequence and complementary to a probe sequence.

As used herein, the term "generic antiprobe" shall refer to an antiprobe comprising a sequence that is complementary to a sequence of a probe but that is not in common with a sequence of the target.

As used herein, the term "universal probe" shall refer to a probe comprising an artificial sequence that is not complementary to any known target sequence unless the target is intentionally appended with a sequence complementary to the universal probe.

As used herein, the term "universal antiprobe" shall refer to an antiprobe comprising an artificial sequence that is complementary to a sequence segment of a universal probe.

As used herein, the term "universal linker" shall refer to a polynucleotide sequence appended to a probe or a primer that is in common with a sequence segment of a universal probe.

As used herein, the term "multiplex reaction" shall refer to a copying or amplification reaction, such as PCR, in which two or more primer sets are employed.

As used herein, the term "multiplex detection" shall refer to the detection of two or more targets in the same sample, preferentially with probes of different color.

In a primary embodiment of the present invention there is provided a probe-antiprobe composition to detect a target sequence, comprising: (i) a polynucleotide probe having a sequence complementary to the target sequence and the first labeling component of a pair of interacting labeling components, and (ii) a polynucleotide antiprobe comprising the second labeling component and a sequence that binds to a partial segment of the probe substantially within or outside of the target complementary sequence of the probe. This general probe-antiprobe composition exhibits two signaling states: a first signaling state when the paired labeling components are in proximity due to the binding of probe and antiprobe and a second signaling state when the labeling components are spatially dissociated due to the binding of probe and target. This composition can detect targets in a sample when probes, antiprobes and targets are hybridized together, whereupon the signaling potential of the composition switches from the first to the second signaling state relative to the frequency of the targets in the sample.

In one aspect of this embodiment, the labeling components of the composition comprise a FRET donor-acceptor pair consisting of a fluorescent donor compound paired with a fluorescent acceptor moiety, wherein the fluorescent acceptor moiety is defined as comprising either a longer wavelength fluorescent compound, a quencher compound, or a guanine-rich sequence segment having about 2 to about 8 guanines; wherein the signaling state of the probe-antiprobe composition is modulated by the relative proximity of the donor and acceptor labeling components. In the case of a pair of fluorescent donor and acceptor moieties, FRET interaction results in a shift in the color emitted, whereas when the acceptor moiety comprises a quencher or a guanine-rich sequence segment, FRET interaction results in absorbance of the donor signaling. In multiple embodiments of the present invention, a synthetic or natural guanine-rich sequence segment comprising about 2 to about 8 guanines can serve as an effective acceptor moiety, although the quenching potential of such components is relatively weak. Similarly, the signaling potential of fluorescent donors paired with fluorescent acceptors or quenchers are quite variable and depend on the specific compounds selected.

In another aspect of this composition, the labeling components are selected from the group consisting of: FAM, TET, HEX, JOE, VIC, ROX, NED, Texas Red, Yakima Yellow, BHQ1, BHQ2, BHQ3, Iowa Black FQ, Iowa Black RQ, TAMRA, DABCYL, ElleQuencher, Eclipse Dark Quencher, Methyl Red, DisperseBlue3, Bodipy 493/503, the Cy dyes Cy2, Cy3, Cy3.5, Cy5, Cy5.5, and Cy7, the AlexaFluor dyes 488, 532, 546, 555, 568, 594, 610, 647, and 680, the PromoFluor dyes 488, 555, 590, 633, 647, and 680, a fluorescent compound, a quencher compound, a color dye compound, a quantum dot, a silver or nanogold compound, and a guanine-rich sequence segment.

In another aspect of this embodiment, the probe comprises a target-specific sequence of about 20 to about 40 bases and the antiprobe comprises a shorter probe-complementary sequence of about 7 to about 20 bases; this probe-antiprobe composition being effective for end-point detection, microarray detection, or real-time PCR detection.

In another embodiment of the general probe-antiprobe composition, the polynucleotide probe is a two-segment probe comprising sequentially: a first labeling component of a pair of interacting labeling components, a first sequence segment complementary to the target sequence, and a generic second sequence segment that does not match or complement any target sequence in the sample. The corresponding antiprobe is a generic antiprobe that comprises the second labeling component of the pair of interacting labeling components and a sequence complementary to the generic second sequence segment of the probe. In this embodiment, when probe and antiprobe are bound together, the paired labeling components are brought into proximity by random coiling. However, when the probe is hybridized to a matching target, the probe will straighten and extend so that the pair of labeling components are spatially dissociated. With this composition, signaling therefore switches from a first signaling state to a second signaling state in proportion to the frequency of the targets.

In another aspect of this embodiment wherein the probe comprises two segments, the labeling components comprise a FRET donor-acceptor pair as defined supra and the labeling configuration of the probe and antiprobe is selected from one of the following: a 5' donor-labeled probe and a 3' or 5' acceptor-labeled antiprobe, a 3' donor-labeled probe and a 3' or 5' acceptor-labeled antiprobe, a 3' acceptor-labeled probe and a 5' or 3' donor-labeled antiprobe, and a 5' acceptor-labeled probe and a 5' or 3' donor-labeled antiprobe.

In another embodiment of the probe-antiprobe composition, the probe and antiprobe components comprise a single polynucleotide labeled with a FRET donor-acceptor pair as defined supra; wherein the polynucleotide comprising a donor-label at one end and an acceptor-label at the other end; wherein the antiprobe sequence at one end is partially complementary to the probe sequence at the other end; wherein the length and sequence of the antiprobe and probe segments are selected so that the Tm between the probe segment and target is about two or more degrees higher than the Tm between the antiprobe segment and the probe segment. With this embodiment, the binding of the shorter antiprobe segment to a portion of the probe sequence comprises a first signaling state and the binding of the longer probe segment to the longer target sequence comprises a second signaling state; wherein the signaling potential of the composition switches from the first to the second signaling state relative to the presence and frequency of the targets. This composition provides highly specific detection of a matching target sequence and avoids the detection of a mismatched target sequence, including a single base mismatch.

In another embodiment of the general probe-antiprobe composition, wherein the probe comprises one sequence segment that is complementary to the target sequence, the length and position of the antiprobe sequence is selected to be partially complementary to the sequence of the probe so that the Tm between probe and target is about two or more degrees higher than the Tm between antiprobe and probe. With this composition, the labeling components comprise a FRET donor-acceptor pair as defined supra and the labeling configuration of the probe and antiprobe is selected from one of the following: a 5' donor-labeled probe and a 3' acceptor-labeled antiprobe; a 3' donor-labeled probe and a 5' acceptor-labeled antiprobe; a 3' acceptor-labeled probe and a 5' donor-labeled antiprobe; a 5' acceptor-labeled probe and a 3' donor-labeled antiprobe; a 5' and 3' donor-labeled probe and a 5' and 3' acceptor-labeled antiprobe; a 5' and 3' acceptor-labeled probe and a 5' and 3' donor-labeled antiprobe; a probe with 5' donor-label and 3' acceptor-label and an antiprobe with 3' acceptor-label and 5' donor-label; a probe with 5' acceptor-label and 3' donor-label and an antiprobe with 3' donor-label and 5' acceptor-label; a probe with a central donor-label and an antiprobe with a central acceptor-label; and a probe with a central acceptor-label and an antiprobe with central donor-label.

In another embodiment of the one segment probe and antiprobe composition described above, the probe serves as a primer/probe wherein the probe sequence comprises a primer sequence. When used to amplify a target sequence, the signaling potential of this primer-probe composition switches from a first signaling state to a second signaling state when each primer/probe is incorporated into an amplified target. In a primary embodiment of this composition, the primer/probe comprises a sequence of about 20 to about 40 bases and the antiprobe comprises a sequence of about 16 to about 22 bases. This composition is suitable for real-time PCR amplification and detection.

In another aspect of the above primer/probe composition, the primer/probe comprises two sequence segments, a labeled generic or universal sequence not complementary to the target sequence, and a 3' target-specific primer sequence, and the labeled antiprobe is complementary to the generic or universal sequence of the primer/probe. When the target is amplified with this two segment primer probe the antiprobe sequence is appended to the amplicon, thus preventing antiprobe binding to the probe, and resulting in a signaling change suitable for real-time detection.

In one embodiment of this primer/probe-antiprobe composition, the primer/probe and antiprobe are modified to further comprise artificial sequences that are inserted between the labeling component and the target-specific sequence of the probe as well as between the labeling component and the target-specific sequence of the antiprobe; wherein the Tm between antiprobe and probe is increased to improve probe-antiprobe binding and/or to improve specificity. Typically, an artificial cytidine-rich segment, comprising one to four cytidines, is inserted next to the fluorescent donor label and a complementary guanine-rich segment is inserted next to the acceptor label.

In another embodiment of the primer/probe-antiprobe composition described above, an antiprobe is not employed and the primer/probe is designed to comprise a self-quenching primer/probe. In this aspect of the invention, the primer/probe comprises sequentially: (i) a fluorescent labeling component; (ii) an inserted artificial cytidine-rich sequence comprising about 2 to about 8 cytidines; and (iii) the 3' primer sequence; wherein the signaling potential of the primer/probe switches from a high signaling state to a low signaling state when it is incorporated into amplified targets due to the formation of a corresponding guanine-rich sequence segment in the strand adjacent to the primer/probe which serves to absorb the fluorescent energy of the label.

In another aspect of this embodiment, a similar detection effect can be achieved by designed the primer/probe as a natural self-quenching primer/probe; wherein the primer/probe sequence location is selected to include one or more cytidines and no guanines near the label end of the probe. While this embodiment has limited sensitivity, it can be sufficiently effective in some target sequences.

In another embodiment of the general probe-antiprobe invention, the composition is modified to provide precise discrimination of small sequence differences within the target sequence such as SNPs or mutant bases or other small sequence variants. In this embodiment the probe comprises a polynucleotide sequence complementary to the target region and one or more labeling components and the antiprobe comprises an unlabeled polynucleotide that is complementary to a partial sequence of the probe. Moreover, the probe and antiprobe sequences are selected to locate the variant base or bases of interest between the ends of the antiprobe sequence and preferably central to the antiprobe sequence. In addition, the length and position of the probe and antiprobe sequences relative to the target sequence are selected to exhibit three Tm levels that differ by about two or more degrees from each other when these components are hybridized together; said Tm levels comprising a high Tm level between the probe and the correct matching target; an intermediate Tm level between the probe and the antiprobe; and a low Tm level between the probe and an incorrect mismatched target. Due to this design, when probes, antiprobes and targets are hybridized together, the binding of the probe and a fully matching target is favored first, the binding of the probe and the antiprobe is favored second, and the binding of the probe and a mismatched target is effectively avoided or prevented even at low hybridization temperatures. Thereby, this composition selectively detects target sequences complementary to the probe and selectively avoids the detection of target sequences not complementary to the probe.

In one aspect of the embodiment described above, the probe is labeled at both ends with a FRET donor-acceptor pair as defined supra and the antiprobe is unlabeled. This composition inhibits mismatch detection, thereby enabling precise detection of targets in situ and precise detection of an internal target site with real-time PCR.

In another aspect of this embodiment, the probe comprises a TaqMan probe or a Molecular Beacon probe and the shorter antiprobe is unlabeled; wherein this composition inhibits mismatch detection and enables more precise real-time PCR amplification and detection with said probes.

In another embodiment of the general probe-antiprobe composition described above, both the probe and antiprobe are preferably labeled with a FRET donor-acceptor pair as defined supra; wherein the labeling configuration is selected from the group consisting of: a 5' donor-labeled probe and a 3' acceptor-labeled antiprobe; a 3' donor-labeled probe and a 5' acceptor-labeled antiprobe; a 3' acceptor-labeled probe and a 5' donor-labeled antiprobe; a 5' acceptor-labeled probe and a 3' donor-labeled antiprobe; a 5' and 3' donor-labeled probe and a 5' and 3' acceptor-labeled antiprobe; a 5' and 3' acceptor-labeled probe and a 5' and 3' donor-labeled antiprobe; a probe with 5' donor-label and 3' acceptor-label and an antiprobe with 3' acceptor-label and 5' donor-label; a probe with 5' acceptor-label and 3' donor-label and an antiprobe with 3' donor-label and 5' acceptor-label; a probe with a central donor-label and an antiprobe with a central acceptor-label; and a probe with a central acceptor-label and an antiprobe with central donor-label.

In a further embodiment of the general probe-antiprobe composition described above, preferably for precise real-time PCR amplification and detection, the probe is designed as an internal probe comprising a sequence complementary to a target region that is positioned between two primer binding sites, and any unlabeled 3' end of the probe or antiprobe is chemically modified to block polymerase extension. This 3' modification is preferably an amino modifier, a spacer or a phosphate.

In another embodiment of the general probe-antiprobe composition, the probe is designed as a universal probe and antiprobe that is used in conjunction with a target specific primer that also comprises a 5' linker that matches the universal probe. This composition thus employs three components: (i) a universal linker/primer consisting of a 5' linker sequence and a 3' primer sequence; (ii) a universal probe comprising a universal primer sequence that substantially corresponds to the linker sequence of the universal linker/primer; and (iii) a universal antiprobe comprising a sequence complementary to a partial segment of the universal probe. The sequences of the universal probe, the universal antiprobe and the linker of the universal linker/primer do not substantially match or complement a sequence in the target sample. The universal probe and antiprobe are preferably labeled with a FRET donor-acceptor pair as defined supra; wherein the labeling configuration preferably comprises a 5' donor-labeled probe and a 3' acceptor-labeled antiprobe or a 3' acceptor-labeled probe and a 5' donor-labeled antiprobe. This composition enables real-time amplification and detection of a specific target sequence with a generic or universal probe.

In another embodiment of the universal probe-antiprobe composition, the universal primer sequence of the probe comprises a sequence that does not match any known sequence in any natural organisms as determined by a BLASTn analysis of the international GenBank database which reports: "no significant sequence similarity found". This universal probe has general utility for any known target sequence.

In another aspect of the universal probe-antiprobe composition, an antiprobe is not employed and the probe comprises a self-quenching universal probe having sequentially: (i) a 5' fluorescent labeling compound; (ii) an inserted artificial cytidine-rich sequence comprising about 2 to about 8 cytidines; and (iii) a 3' universal primer sequence; wherein the signaling potential of the universal probe switches from a high signaling state to a low signaling state when it is incorporated into amplified targets.

In another aspect of the universal probe-antiprobe composition, multiple primer/probes are employed together that share a common universal probe and antiprobe. This embodiment is designed to detect multiple target sites in a sample by real-time PCR and to prevent false negative tests due to small sequence variations that may occur in a target site. This composition comprises a common universal probe and antiprobe and two or more universal linker/primers; wherein the universal linker/primers comprise different primer sequences specific to different target sites and a common universal linker; wherein multiplex amplification of the different targets with the common universal probe will produce a combined detection signal such that false negative tests can be avoided.

In a further aspect of the universal probe-antiprobe composition, the composition employs multiple linker/primers for different targets, and different universal probes that providing separate signaling for different targets. This embodiment is designed to separately detect multiple target sites in a real-time PCR assay and to thereby avoid false positive tests. The composition comprises two or more universal probes and antiprobes and two or more universal linker/primers; wherein the universal linker/primers comprise different primer sequences specific to different target sites as well as different universal linkers specific to the different universal probes and antiprobes; wherein each universal probe and antiprobe pair comprise different labeling, preferably with different colors; and wherein multiplex amplification of different targets with different universal probes will produce a pattern of two or more signals that confirm detection such that false positives can be avoided.

In another aspect of the above embodiment, false negative or false positive tests are similarly avoided by multiplex detection with the self-quenching universal probe. In these compositions, false negative tests are avoided by employing together a common self-quenching universal probe with two or more universal linker/primers that prime, amplify and label different targets with the same combined signal; and false positive tests are avoided by employing together two or more self-quenching universal probes and universal linker/primers that prime, amplify and label different targets with different signals.

Another aspect of the invention is embodied in a general method for employing the general probe-antiprobe composition; wherein target detection comprises: (a) providing the polynucleotide probe and antiprobe at concentration ratios in the range of about 1:1 to about 1:2; (b) hybridizing the target and the probe-antiprobe composition together; and (c) detecting changes in signaling to determine the presence and frequency of the target.

In another embodiment of the general probe-antiprobe method, a method is provided for detecting different target sequences in an array format, comprising: (a) providing an array of target-specific probes that are labeled with a donor or acceptor moiety and that are attached to the substrate at known target-specific locations; and providing known quantities of matching antiprobes that are labeled with a paired acceptor or donor moiety; (b) hybridizing the antiprobes and the unlabeled targets of interest to the fixed probes in the array; and (c) detecting signaling changes per probe position in the array to indicate target frequency.

In related embodiments of the array-based probe-antiprobe method, the method comprises: (a) providing an array of two segment probes fixed to a substrate and a quantity of generic antiprobes; wherein the probes and antiprobes are labeled with a donor-acceptor pair; or (b) providing an array of one segment probes fixed to a substrate and a quantity of target-specific antiprobes; wherein the probes and antiprobes are labeled with a donor-acceptor pair.

In another aspect of the invention a method is described to improve quantification with real-time PCR assays, wherein the self-quenching primer/probe or the self-quenching universal primer/probe compositions are employed at a concentration that exhausts the available primer/probes within the thermal cycling periods provided. This method comprises: (a) providing the self-quenching probes at a highly restricted concentration; preferably in the range of about 10% or less of the normal primer concentration; (b) calculating the target copies that can be made with the restricted quantity of primer/probes; (c) amplifying the targets with the starved primer/probe and a second primer; (d) monitoring and examining the signaling profile to determine the stages and quantity of target amplification that occurred, wherein the presence of a unique descending signaling curve, herein described as a Roller-Coaster curve, provides a quantitative indicator of the cycling time point when a defined quantity of target product was made, wherein the signature profile of this Roller-Coaster signaling curve comprises three or four phases: (i) a level, high, background signal, (ii) a rapidly descending signal, (iii) a low point or nadir in signaling, and (iv) optionally, a gradually re-ascending signal. With this method, the nadir in the signaling curve marks the cycling time point when the number of primer/probes provided is exhausted, thereby providing a quantitative indicator of the amplified targets generated.

In a primary embodiment of the above method, the self-quenching primer/probe is provided in the concentration range of about 10 nM to about 50 nM, preferably at 20 nM, such that in a 25 μl reaction volume the resulting nadir in the signaling curve is indicative of the amplification time point when approximately $3 \times 10^{11}$ copies of the product are present.

In another embodiment of the probe-antiprobe method for real-time PCR or related amplification procedures, double signaling or two-color signaling is achieved with a method comprising: (a) providing a pair of forward and reverse primer/probes consisting of a primer/probe, a self-quenching primer/probe, a universal primer/probe, or a self-quenching universal primer/probe; wherein both the forward and the reverse primer/probes of each pair are labeled with the same color or a different color; wherein universal probes of different color also comprise different universal sequences; and (b) detecting the signaling; wherein double signaling provides earlier and more sensitive detection; and wherein two color signaling provides confirmation of correct target amplification and avoids false positive tests.

In another embodiment of the universal probe-antiprobe composition, amplification and detection of the target is preferentially achieved with a universal primer/probe that substantially comprises a sequence that is: SEQ ID NO: 1 to 16, wherein said sequence is not significantly similar to any known genomic DNA sequence or expressed mRNA sequence in the GenBank international database as previously determined by BLASTn analysis, and the linker of the universal linker/primer comprises a substantial segment of the universal primer sequence, and preferentially comprises about 20 bases.

In another aspect of the probe-antiprobe composition, for the precise detection and/or discrimination of *M. tuberculosis* and *M. avium* (paratuberculosis) species or samples; the paired probe and antiprobe components are selected to substantially comprise sequences that are SEQ ID NO 17 to 24 or their complements.

In another aspect of the probe-antiprobe composition, for the precise detection and/or discrimination of HIV-1 at RT site K103N in which the drug resistant 103N mutant results from a single base change, T-G, the paired probe and antiprobe components are selected to substantially comprise sequences selected from the group consisting of: SEQ. ID. NO. 25 to 28 or their complements.

Provided herein are general compositions and methods for detecting single or multiple polynucleotide target sequences by employing novel probe and antiprobe compositions and detection strategies in various liquid and solid phase detection platforms such as microarrays, real-time PCR, and fluorescent plate readers. The probe and antiprobe compositions of the present invention can be employed with both solid-phase and liquid-phase detection formats and can be applied to a myriad variety of diagnostic and research applications. The present invention is an improvement to microarray detection since current methods entail considerable time, cost and difficulty in labeling the probes and processing the chips after hybridization. Surface bound probes are provided that function as a molecular switch that would automatically light up when the target sequence was detected. This approach eliminates the need for difficult and delicate wash steps as well as the cost and burden of labeling the DNA or RNA targets of interest.

More specifically, and without being limiting, probe/antiprobe compositions may be any composition as described more fully herein in the methods utilizing them. Table I identifies the specific sequences useful in the methods and compositions described herein, however such listing should not be considered limiting.

TABLE 1

| SEQ ID | SEQUENCE | BPs | LABEL | TYPE |
|---|---|---|---|---|
| 1 | CCCTATCGCT ACGTAGACTA GACGTTC | 27 | 5'-fluor | universal probe |
| 2 | CCTAGACCTA CGACATAGGT ACCCTAC | 27 | 5'-fluor | universal probe |
| 3 | CTACAATACG TTAACGCCTA AGAGTAG | 27 | 5'-fluor | universal probe |
| 4 | CATAGAACTA GCACGCTACG TACTAGG | 27 | 5'-fluor | universal probe |
| 5 | CCCCCCCTCT CCCTTCTTCG AACTTACTC | 29 | 5'-fluor | universal probe |
| 6 | CCCCCCCTCC TACGACATAG GTACCCTAC | 29 | 5'-fluor | universal probe |
| 7 | CCCTAGCGCT ACGTAGACTA TTTCACG | 27 | 5'-fluor | universal probe |
| 8 | CCCTTACGCA TCGACTAGGT AGACTTC | 27 | 5'-fluor | universal probe |
| 9 | CCCGTAGACT ACACGTTCCG CTATTAC | 27 | 5'-fluor | universal probe |

TABLE 1-continued

| SEQ ID | SEQUENCE | BPs | LABEL | TYPE |
|---|---|---|---|---|
| 10 | CCCGACTACG TACGCTAGAC GTATTTC | 27 | 5'-fluor | universal probe |
| 11 | CCCTACGTAG ACCGCTAGTT CACGTAT | 27 | 5'-fluor | universal probe |
| 12 | CCCTAGACGT TCTATTACGT AGACCGC | 27 | 5'-fluor | universal probe |
| 13 | CCCATAATCC TACTGATCGC GTGCAAG | 27 | 5'-fluor | universal probe |
| 14 | TACGTTAACG CCTAGCAAGA GTAA | 24 | 5'-fluor | universal probe |
| 15 | CAATTGCGGA TTCACGTTAT GATC | 24 | 5'-fluor | universal probe |
| 16 | TAGCAAGAGT AATACGTTAA CGCC | 24 | 5'-fluor | universal probe |
| 17 | CATGTCTTGT GGTGGAAAGC | 20 | 5'-donor 3'-blocked | internal MTB probe |
| 18 | CATGTCTTCT GGTGGAAAGC | 20 | 5'-donor 3'-blocked | internal avium probe |
| 19 | TTCCACCACA AGACATG | 17 | 3'-acceptor | MTB antiprobe |
| 20 | TTCCACCAGA AGACATG | 17 | 3'-acceptor | avium antiprobe |
| 21 | TAGGACCACG GGATGCATGT CTT | 23 | 5'-donor 3'-blocked | internal MTB probe |
| 22 | TAGGACCTCA AGACGCATGT CTT | 23 | 5'-donor 3'-blocked | internal avium probe |
| 23 | ATGCATCCCG TGGTCCTA | 18 | 3'-acceptor | MTB antiprobe |
| 24 | ATGCGTCTTG AGGTCCTA | 18 | 3'-acceptor | avium antiprobe |
| 25 | CTGTTACTGA TTTTTTCTTT TTTAACC | 27 | 5'-donor 3'-blocked | 103K probe |
| 26 | CTGTTACTGA TTTGTTCTTT TTTAACC | 27 | 5'-donor 3'-blocked | 103N probe |
| 27 | AAAAAGAAAA AATCAGTAAC AG | 22 | 3'-acceptor | 103K antiprobe |
| 28 | AAAAAGAACA AATCAGTAAC AG | 22 | 3'-acceptor | 103N antiprobe |
| 29 | TCAGGAACCG CCAATCAGCC GATCCGGCTC GGCGTGCATG TC | 42 | 5'-fluor | probe |
| 30 | GGTTCCTGA | 9 | 3'-quencher | antiprobe |
| 31 | CGGATCGGCT GATTGGCGGT TCCTGACAGA ACATCG | 36 | | target |
| 32 | GACATGCACG CC | 12 | 3'-quencher | antiprobe |
| 33 | TCAGGAACCG CCAATCAGCC GGCGTGCATG TC | 32 | 5'-fluor | probe |
| 34 | GTACCCTACC GTGTGTGGCC GCGAGACACT CTT | 33 | 5'-fluor | probe |
| 35 | GTAGGGTAC | 9 | 3'-quencher | antiprobe |

TABLE 1-continued

| SEQ ID | SEQUENCE | BPs | LABEL | TYPE |
|---|---|---|---|---|
| 36 | CGTGTGGCCG CGAGACACTC TTGGCGTGCA T | 31 | 5'-fluor | probe |
| 37 | ATGCACGCC | 9 | 3'-quencher | antiprobe |
| 38 | TTTAAGAGT GTCTCGCGGCC ACACGAAAGT AGGGTACCTA TGT | 43 | | target |
| 39 | AGCGTCCAT CCCCCGACTGG GCGTGCATGT C | 31 | 5'-fluor | probe |
| 40 | AGCGTCCAT CCCCCGACTGC CAGGAGCAGA GATCGGCGTG CATGTC | 46 | 5'-fluor | probe |
| 41 | ATGGACGCT | 9 | 3'-quencher | antiprobe |
| 42 | TCGAATTAAT CCACATGCTC CGGGCGTGCA T | 31 | 5'-fluor | probe |
| 43 | TTAATTCGA | 9 | 3'-quencher | Antiprobe |
| 44 | TTTTGGCGGC GGACTGATCG GTGGCGTGCA T | 31 | 5'-fluor | probe |
| 45 | CCGCCAAAA | 9 | 3'-quencher | antiprobe |
| 46 | CGGATCGGCT GATTGGCGGT TCCTGACAGA ACATCG | 36 | | target |
| 47 | GGCGTGCATG TCTCAGGAAC CGCCAATCAG CC | 32 | 5'-fluor | probe |
| 48 | GGCGTGCATG TCTCAGGAAC CGCCAATCAG CCGATCCGGC TC | 42 | 5'-fluor | probe |
| 49 | GGCTGATGG | 9 | 3'-quencher | antiprobe |
| 50 | GAGCCGGAT | 9 | 3'-quencher | antiprobe |
| 51 | GACATGCACG CC | 12 | | primer |
| 52 | TGGCAGCCTG TGGGCCAGGA CG | 22 | 5'-fluor | primer/probe |
| 53 | TGGCAGCCTG TGGGCCAGGA CC | 22 | 5'-fluor | primer/probe |
| 54 | CTGGCCCACA GGCTGCCA | 18 | 3'-quencher | antiprobe |
| 55 | TCTCGACTCC AGCTGTAGGT T | 21 | | primer |
| 56 | CCCCCCCCTG GCAGCCTGTG GGCCAGGACC | 30 | 5'-fluor | primer/probe |
| 57 | CCCCCCCCCC ACATCCAGTA CTGTTACTGA TTCT | 34 | 5'-fluor | primer/probe |
| 58 | AAGGCCAGTC CAGCCAATGA CCT | 23 | 5'-fluor | primer/probe |
| 59 | TCATTGGCTG GACTGGCCTT | 20 | 3'-quencher | antiprobe |
| 60 | AGAAGGCCAG TCCAGCCAAT GACCTCTGTT | 31 | | Taqman probe |
| 61 | GCCGGAATGG TCTTACATAG TG | 22 | | primer |
| 62 | GCCGGAATGG TCTTACATAG TG | 20 | | primer |
| 63 | TCTTCATAGT CATTGAAATC CCCTG | 25 | | primer |
| 64 | CCCCCCCCCC ACATCCAGTA CTGTTACTGA TGGG | 34 | 5'-fluor | primer/probe |
| 65 | TTCATCAATC CTATCTAATC TTGCA | 25 | 5'-fluor | primer/probe |
| 66 | TTAGATAGGA TTGATGAA | 18 | 3'-quencher | antiprobe |
| 67 | CAATGAAGAA GAATCCAGCT ATTC | 24 | | primer |
| 68 | CCCCCCCTT CATCAATCCT ATCTAATCTT GCT | 33 | 5'-fluor | primer/probe |
| 69 | CCCCCCCCAA TGAAGAAGAA TCCAGCTATT C | 31 | 5'-fluor | primer/probe |
| 70 | GCTACGTAGA CTAGACGTTC TGCCGGAATG GTCTTACATA GTG | 43 | | linker/primer |
| 71 | CCCTGGGTAA CAGAGGTCAT TG | 22 | | primer |
| 72 | GCTACGTAGA CTAGACGTTC GTATGCCATT CCACAACATA CACC | 44 | | linker/primer |
| 73 | GTCGCAAGGA CTAATCTGTT TGA | 23 | | primer |
| 74 | GCTACGTAGA CTAGACGTTC GAGGAAATAA GTGGAGTAAA ATTGGA | 46 | | linker/primer |
| 75 | CCATGATTGC CAGTGCTAGG | 20 | | primer |
| 76 | GTATGCCATT CCACAACATA CACC | 24 | 5'-quencher | primer/probe |
| 77 | TATGTTGTGG AATGGCATAC | 20 | 3'-fluor | antiprobe |
| 78 | CCCCCCCCCC ACATCCAGTA CTGTTACTGA TTGG | 34 | 5'-fluor | primer/probe |
| 79 | TTGGGCCTGA AAATCCATAC AAT | 23 | | primer |
| 80 | CCACATCCAG TACTGTTACT GATTTG | 26 | 5'-fluor | primer/probe |
| 81 | TAACAGTACT GGATGTGG | 18 | 3'-quencher | antiprobe |
| 82 | TCAAGACTTC TGGGAAGTTC AA | 22 | | primer |
| 83 | CCCCCCCCCC ACATCCAGTA CTGTTACTGA TTTG | 34 | 5'-fluor | primer/probe |
| 84 | CCCCCCCCCC ACATCCAGTA CTGTTACTGA TTGG | 34 | 5'-fluor | primer/probe |
| 85 | TAGTCTACGT AGCGATAGGG | 20 | 3'-quencher | antiprobe |

These novel DNA detection switch (DDS) probe-antiprobe mechanisms thus comprise a new general method to modulate probe signaling relative to target frequency. In the primary version of this probe-antiprobe system, the probe comprises a sequence complementary to a target and the shorter antiprobe comprises a sequence that binds to a partial segment of the probe generally adjacent to the label. The alternate version is based on a two segment probe that comprises a target-specific segment and a generic tail segment, and employs a short antiprobe that binds only to the generic tail segment.

In one version of the DDS probe-antiprobe system, the antiprobe is complementary to a partial segment of the probe, targeting the sequence immediately adjacent to the fluorescent label. Typically, such antiprobes comprise a sequence that is about 30 to 60 percent of probe length. Thus, if probes and matching antiprobes are mixed together under standard nucleic acid hybridization conditions, the 5' fluorescent donor labeled end of the probe and the 3' acceptor-labeled end of the antiprobe would be brought together, thereby diminishing or shifting fluorescent emissions. However, whenever targets complementary to the probe are available, they would be greatly advantaged in binding to the probe due to the relatively short length of the antiprobe sequence. Consequently, the binding of a target to a probe automatically prevents, displaces or inhibits antiprobe binding, thereby changing the fluorescent emission potential of the probe.

Because this molecular switch is designed to be highly biased towards binding the target vs. the antiprobe to the probe, it essentially works one way, turning on probes whenever matching targets are present. This mechanism contrasts with the competitive equilibrium that would result if both the probe and antiprobe had equivalent lengths of target-specific sequences. Because of this one-way switch mechanism, very similar effects can be achieved with the present invention either by mixing targets, probes and antiprobes together simultaneously or by combining them separately on a sequential basis. Thus, the changes in fluorescent signaling that result from this automatic molecular switch will correspond to the number of targets present in the sample.

In a modified version of the probe-antiprobe system described above, the probes and antiprobes are designed with a short universal sequence segment near the fluor-labeled end of the probe, and with a matching universal sequence on the antiprobe. In this embodiment, the targets are made with a short sequence segment on one end that corresponds to the universal sequence on the antiprobe. Such targets are achieved by copying all targets with a primer that appends a universal sequence. With such probes employed in an array format, only one universal antiprobe component is required to quench a series of different probes employed in the array.

Another version of the DDS probe-antiprobe system is based on two segment probes. The probe comprises a first sequence segment adjacent to the label that is complementary to the target and a second segment distant from the label which is complementary to a generic antiprobe and not the target. When such probes and antiprobes are mixed and bound together, in the absence of complementary targets, the relaxed single-stranded target-specific segment of the probes can freely bend or coil, thereby bringing the labeled ends of the probe and antiprobe in close proximity, wherein the fluorescent emission potential of the probes is significantly diminished or shifted. However, when complementary targets are available to bind to these probes, the probes will straighten and extend, moving the labeled ends of probe and antiprobe apart, so that the fluorescent emission potential of the donor-labeled probe is released. Since the antiprobe does not bind to the target-specific segment of the probe, target binding will not displace or prevent antiprobe binding.

Nonetheless, this detection mechanism also functions automatically as targets are added to a mix of probes and antiprobes, and thus, all components can be mixed together at the same time or sequentially. Since this alternative probe-antiprobe mechanism also functions as a one-way molecular switch biased towards target binding, both systems can be employed effectively for the same or similar targets. Indeed, some two segment probes were made and tested with both types of antiprobes and gave similar results. Because these major embodiments of this probe-antiprobe system work similarly and because both mechanisms can work with a common probe, these probe systems are classed and described together as DNA detection switch (DDS) compositions.

Alternatively, the labeling of probe and antiprobe can be reversed such that the probe is labeled with an acceptor moiety and the antiprobe is labeled with a fluorescent donor compound. When such reversed labeling is employed with target-specific antiprobes, target binding to the probe displaces the donor-labeled antiprobe so that donor emissions are released. When such reversed labeling is employed with generic antiprobes binding to the tail end of the probes, target binding to the target-specific end of probe straightens and extends it, putting distance between the labeled ends of probe and antiprobe so that donor emissions are released.

The DDS methods and compositions described herein enable real-time PCR detection by increasing the relative size of the target-specific antiprobe to about 75 to 95 percent of probe length. This relative length enables antiprobes to bind unused probes at the higher thermal cycling conditions that are typically employed for PCR amplification and real-time detection. In addition, the labeled probe may serve as a primer, thereby eliminating one amplification/detection component.

The following examples are given for the purpose of illustrating various embodiments of the invention and are not meant to limit the present invention in any fashion.

Example 1

Array Detection of DDS Probes with Shorter Antiprobes

This example demonstrates that target-specific DDS probes and antiprobes can be applied and detected on a microarray platform with an array scanner. FIG. 7A shows detection of hand-printed samples in three conditions: the probe alone; the probe plus a matching quencher antiprobe; and the probe, the antiprobe and the target mixed together. The probe is complementary to a 26 base long segment of gene Rv3877 of *M. tuberculosis* (MTB). It has FAM fluorescent labeling on the 5' end, it comprises SEQ ID NO: 29 (5' TCA GGA ACC GCC AAT CAG CCG ATC CGG CTC GGC GTG CAT GTC) which comprises that target segment and a twelve base segment at the 3' to bind a target-independent antiprobe (for other experiments). The antiprobe employed for this experiment is complementary to nine target-specific bases at the 5' end of the probe, is labeled with the quencher BHQ1 at its 3' end, and comprises SEQ ID NO: 30 (GGT TCC TGA). This antiprobe will put the quencher molecule in close proximity to the fluorescent label of the probe. A synthetic oligonucleotide comprising SEQ ID NO: 31 (CGG ATC GGC TGA TTG GCG GTT C CT GAC AGA ACA TCG) represents the Rv3877 target sequence.

The samples were prepared with 2×SSC final buffer conditions in a total volume of 5 ul, wherein the probe had a final concentration of 1 uM, the antiprobe 2 uM (when present), and the target 1 uM (when present). The components were mixed and held at room temperature for 2 minutes before applying to the chip. The chips were read with a microarray scanner (GSI Lumonics 5000, Perkin Elmer Instruments, Inc.). Each of the dots shown in FIG. 7A depicts an aliquot of 0.2 ul per dot. The three columns of dots on the chip comprise the three conditions described above, going left to right: 1) dots of the fluor-labeled probe alone—which is brightly fluorescent, 2) dots comprising a mix of the labeled probe and the quencher antiprobe—wherein fluorescence is greatly diminished, and 3) dots comprising a mix of the fluor-probe, the antibody quencher and the target sequence—wherein fluorescence is greatly restored since the target displaces or prevents the binding of the antiprobe to the probe.

FIG. 7B shows similar results with DDS probes printed on microarray substrates with a pin-based spotter (Gene Machines, Inc.). The three panels shown are a segment of an array at three time points: left panel=probes for Rv0577 (upper 8) and Rv3877 (lower 8), middle panel=probe+quencher for Rv3877 only, right panel=probes+quencher and target for Rv3877 only. The signal decreases with the quencher added and is restored with the target added.

Example 2

End Point Detection of DDS Probes with a Fluorescent Plate Reader

This example illustrates quantitative detection of a oligonucleotide target representing the Rv3877 gene of *M. tuberculosis*. Two DDS probe-antiprobe combinations are tested, with two tests employing the same probe of Example 2. In one case, the 5' fluorescent-labeled probe is combined with a short antiprobe that binds to the 5' target-specific end —Type A probes/antiprobes. In the other case, the same probe is combined with a short antiprobe that binds to a generic non-target-specific 3' tail segment at some distance from the labeled end of the probe—Type B probes/antiprobes. One version of these probes again comprises SEQ ID NO 29 which includes a 26 base target-specific segment, while the target-specific antiprobe comprises SEQ ID NO 30, and the generic antiprobe comprises SEQ ID NO 32. The target is again represented by an oligonucleotide comprising SEQ ID NO 31. An alternate version of the probe is also employed that has a 20 base target-specific segment and comprises SEQ ID NO 33. These probes are labeled with FAM fluorescence at their 5' ends while the antiprobes are labeled with the quencher BHQ1 at their 3' ends. The target-specific antiprobe is 9 bases long and the generic antiprobe is 12 bases long. The samples were again prepared in 5 ul volumes with 2×SSC buffer conditions. The concentrations of the probes and the targets were at 100 nM and the antiprobes were at 200 nM. The components were mixed in a small PCR tube, heated to 92° C. for 2 minutes, ramped to 50° C. for 2 minutes and cooled to room temperature for 2 minutes before reading in a fluorescent plate reader.

The results are shown in FIG. 8 wherein the first set of 3 adjacent bars show the use of the 20 base target-specific probe and the target-specific antiprobe. The gray bar shows the probe alone, the dark bar shows the probe and antiprobe, and light bar shows the probe, antiprobe and target mixed together. The second set of 3 bars shows the same conditions but using the probe with the 30 base target-specific segment. Moving right on the graph to position 4, that set of 3 bars shows the same conditions again, but using a generic antiprobe and the probe with a 20 base target-specific segment. Moving right again to position 5, the last set of 3 bars shows the same conditions again but using a generic antiprobe and the probe with a 26 base target-specific segment. As can be seen, each test condition shows high fluorescent signaling with the probe alone, greatly reduced signaling with the antiprobe added, and significant signal restoration with the target added. The resulting signal level reflects the presence and frequency of the target.

Example 3

Quantified Target Detection with DDS Probes and a Fluorescent Plate Reader

This example shows the capacity of DDS probes for quantitative detection of target frequency with both Type A and B probes/antiprobes. The bar graph of FIG. 9 depicts the signaling levels read with a fluorescent plate reader for each tube in the experiment, each of which represented a different set of conditions wherein the first bar (gray) of each pair indicates Type A probe/antiprobe, and the second bar (dark) of each pair indicates Type B probe/antiprobe. The probes and targets all comprise a segment of the human Rab9 gene. The same target was used for both probes, but the probes detect slightly different sequences. Type A probe and antiprobe comprise SEQ ID NO 34 and 35, respectively. Type B probe and antiprobe comprise SEQ ID NO 36 and 37, respectively. The common target comprises SEQ ID NO 38. The probes were 5' labeled with FAM and the antiprobes were 3' labeled with BHQ1.

The test samples were prepared with final concentrations of probe at 125 nM, of antiprobe at 250 nM, and with target at 0, 25, and 50 nM. All tubes were prepared with a 20 ul final volume with standard PCR buffer conditions (10× buffer at 1:10), and the tubes were all heated to 92 degrees C. for 2 min, ramped to 50 degrees C. for 2 minutes and ramped again to 23 degrees C. and then read. The gray bars of each pair reflect a test of Type A probe-antiprobe conditions with a target-specific antiprobe. The dark bars reflect a test of Type B probe-antiprobe conditions with a generic antiprobe. The results depicted in FIG. 9 show left to right, high signaling levels with the probe alone (position 1), negligible signaling with the quencher alone (position 2), somewhat higher signaling with the probe and antiprobe mixed (position 4), and stepped up higher signaling with 25 nM of target (position 5) and 50 nM of target (position 6). Thus, both probe types provide similar quantitative indicators of target frequency.

Example 4

Comparative Tests of DDS Probes for Target Quantification

Additional experiments with the same Type A and B probes, antiprobes and the Rab9 target of example 4 were conducted over a series of target concentrations ranging in graded steps up to the level of probe concentration and using the same heating and cooling conditions before signal measurement with a fluorescent plate reader. FIG. 10A shows a test series with the target concentrations ranging from zero up to 125 nM, with the probe concentration set at 125 nM, and with the antiprobe concentration set at 250 nM. FIG. 10B shows a longer test series with target concentrations ranging from zero up to 250 nM, with the probe concentration set at 250 nM and the antiprobe concentration set at 500 nM. Again the first bar (gray) of each pair shows Type A probes/antiprobes, and the second bar (dark) of each pair shows Type B probes/antiprobes. The Type A probes/antiprobe show a somewhat more linear response vs. the Type B probes/antiprobes at the high end of target concentration, but these small differences may not be important to regular testing conditions.

Example 5

Tests of Different Length DDS Probes

Additional experiments were conducted comparing Type A and B probes of different size and employing two sequence segments of MTB genes Rv3877 and Rv3120 as molecular targets. The bar graph of FIG. 11 shows the results from an experiment using eight sets of different probe and target conditions and measuring three conditions per set. The eight sets go left to right, with three adjacent bars per set showing: a) the probe alone (gray bar), b) the probe plus antiprobe (dark bar), and c) the probe plus antiprobe plus target (light bar). The first four sets employed a target-specific antiprobe which binds adjacent to the fluor end of the probe, while the second four sets used a generic antiprobe which binds at a distance from the fluor end of the probe. The probes employed match a 20 and 26 base segment of Rv3877 (SEQ ID NO: 33, 29) and a 19 and 33 base segment of Rv3120 (SEQ ID NO: 39, 40); the target-specific antiprobe for both Rv3877 probes comprise SEQ ID NO: 30, the target-specific antiprobe for both Rv3120 probes comprise SEQ ID NO: 41, and the generic antiprobe for all 4 probes comprise SEQ ID NO: 32. The degree of fluor-signal quenching is slightly greater with the target-specific antiprobe. The relative size of the long vs. short probes used here does not seem to make a consistent difference in sensitivity.

Example 6

DDS Detection with Raw PCR Products

Further end-point detection studies with DDS probes were made using unpurified, raw PCR products after 0, 10, 20 or 30 cycles of amplification of two segments of the MTB genes 16s and Rv0577. FIG. 12A is a photo of the gel showing these PCR products with the 16s bands on the left and the Rv0577 bands on the right. The FIG. 12B bar graph shows detection with DDS probes and short target-specific antiprobes when mixed with 5 ul of PCR product or the successive addition of further 5 ul aliquots of the PCR product. The 16s probe and antiprobe comprise SEQ ID NO: 42, 43, and the Rv0577 probe and antiprobe comprise SEQ ID NO: 44, 45. Both the gel images and the DDS probes show that these amplifications were largely saturated at 20 cycles and there was little further increase in product at 30 cycles. It is also apparent that only 5 ul of raw PCR product is needed to assess the amplification frequency with this DDS method.

Example 7

End Point Detection with Reverse-Labeled DDS Probes

Further studies were conducted using reverse-labeled Type A and B probes to the Rv3877 gene, wherein the probes were labeled with a quencher compound and the target-specific and generic antiprobes were labeled with a fluorescent compound. Test conditions: 2×SSC buffer, each component at 1 uM final conc. mixed at RT, no heat. Here, binding of the probe to the target (SEQ ID NO: 46) releases the fluorescent signaling of the antiprobe which is displaced—either from binding to the probe, in the case of a target-specific antiprobe, or moved away from the quencher, in the case of a generic antiprobe.

The bar graphs of FIG. 13 show 4 sets of 3 bars each, with each bar set indicating left to right, a gray bar showing the probe alone, a dark bar showing the probe plus antiprobe, and a light bar showing the probe, plus antiprobe, plus target. Again the signal goes down with the antiprobe added, and it rises again with the target added to the mix. The bar sets at positions 1 and 2 indicate Rv3877 probes with a target-specific length of 20 and 26 bases, respectively (SEQ ID NO: 47, 48), and with a target-specific antiprobe (SEQ ID NO: 49, 50). The bar sets at positions 4 and 5 show the same probes, respectively, but in this case the antiprobe is generic and binds to the tail end of the probe (SEQ ID NO: 51). All probe and antiprobe configurations show essentially similar target detection potential.

Example 8

Detection of PCR Products Vs. Oligo Targets with Reverse DDS Probes

Similar effects were observed in measuring raw PCR products with reverse DDS probes. The reverse-labeled probe with a 26 base target-specific segment used in example 7 (SEQ ID NO: 48) is again employed in combination with a generic antiprobe (SEQ ID NO: 57) and with two alternate targets: a synthetic oligo target representing Rv3877 of MTB (SEQ ID NO: 31) and a PCR amplicon of the Rv3877 gene segment from genomic mtb DNA. The test conditions were similar to the previous examples with the probes, antiprobes and targets mixed in a small PCR tube and subjected to heating and cooling before detection with a fluorescent plate reader (92 degree C. 2 min, then 50 degrees C. 2 min, then room temperature). However, the PCR target comprised 10 µl of an amplification reaction that was dried down and combined with the same probe and antiprobe components in 2×ssc buffer conditions. The bar graph of FIG. 14 shows these results with the first set of three adjacent bars at the left showing: a) the probe alone (gray bar), b) the probe plus antiprobe (dark bar), and c) the probe plus antiprobe plus target (light bar). The three adjacent bars at the right show the same three conditions, but with the PCR product as the target sample. Again the signal is high with the probe alone (gray bar), it diminishes greatly with probe and antiprobe mixed (dark bar), and it is largely restored when the target is added (light bar).

Example 9

DDS Probes for Real-Time PCR Detection of Single Nucleotide Polymorphisms (SNPs)

Figure 15:
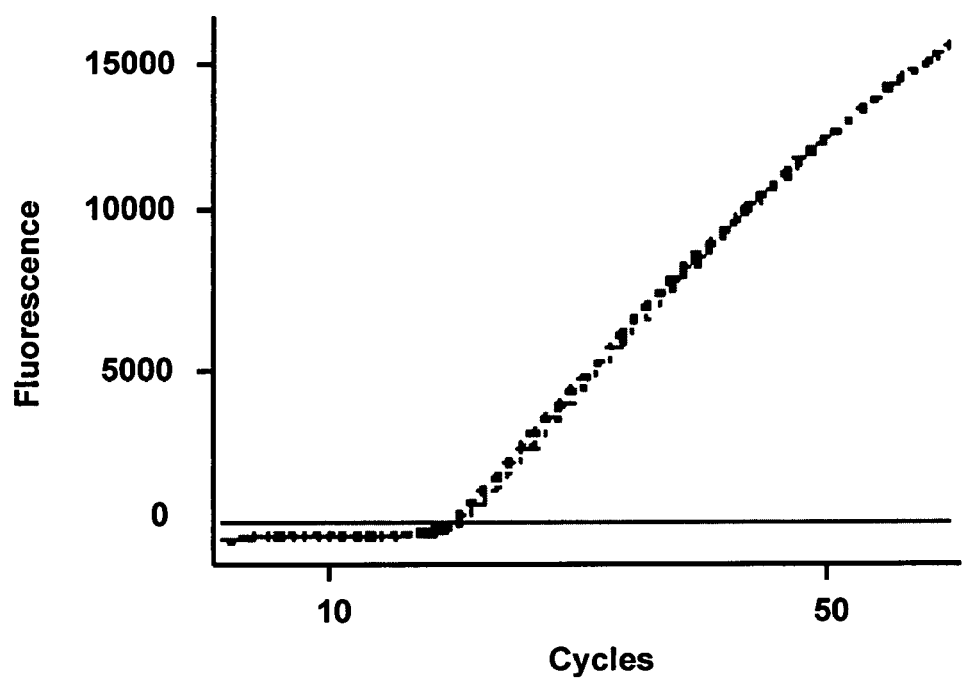
FIG. 15 depicts real-time PCR amplification curves for two human IL-12 SNP sites using DDS primer/probes and antiprobes. Incorporation of the primer/probe releases fluorescence by displacing the quencher antiprobes. Selective primer extension enables differential amplification based on single base differences between two SNP variants. See Example 9.

Experiments to demonstrate the use of DDS probes for real-time SNP detection were generally based upon using the probe as a primer and upon using target-specific antiprobes that were significantly extended, typically to a size of about 18 to 22 bases. This contrasts with the shorter antiprobes 9 to 15 bases long that are typically used for end point detection. longer antiprobes are needed for real-time PCR to ensure that floating primer/probes are bound and quenched by complementary antiprobes during the PCR annealing step when signal measurements are generally made. In this specific example, the primer/probe is designed so that the 3' end comprises the SNP specific base, so that correct real-time hybridization and extension of that primer will selectively amplify the SNP target of interest. The real-time PCR curves illustrated by FIG. 15 show the use of genomic templates containing the human IL-12 gene, with and without a SNP variant at position aa378. Two fluorescent-labeled (FAM) primer/probes for the wild and mutant aa378 SNP were employed (FFN-22: SEQ ID NO: 52, and FFM-22: SEQ ID NO: 53) along with a common antiprobe (Q18: SEQ ID NO: 54) (BHQ1-labeled) and a common reverse primer (SEQ ID NO: 55). FIG. 15 shows real-time detection of both variants, wherein the curve with round dark markers indicates amplification of the wild variant with primer/probe FFN-22, and wherein the curve with square gray markers indicates amplification of the mutant variant with primer/probe FFM-22. each curve is the product of a separate amplification in a separate tube, with both signals rising sharply at about 18 cycles due to similar template quantities. Thermal cycling conditions were initially at 95 degrees C. for 3 min, followed by 60 PCR cycles of denaturation, annealing and extension, respectively, at 95 degrees 10 sec, 53 degrees 30 sec, and 72 degrees 15 sec.

Example 10

Real-Time PCR Detection with Inverse DDS Probes

Figure 16:
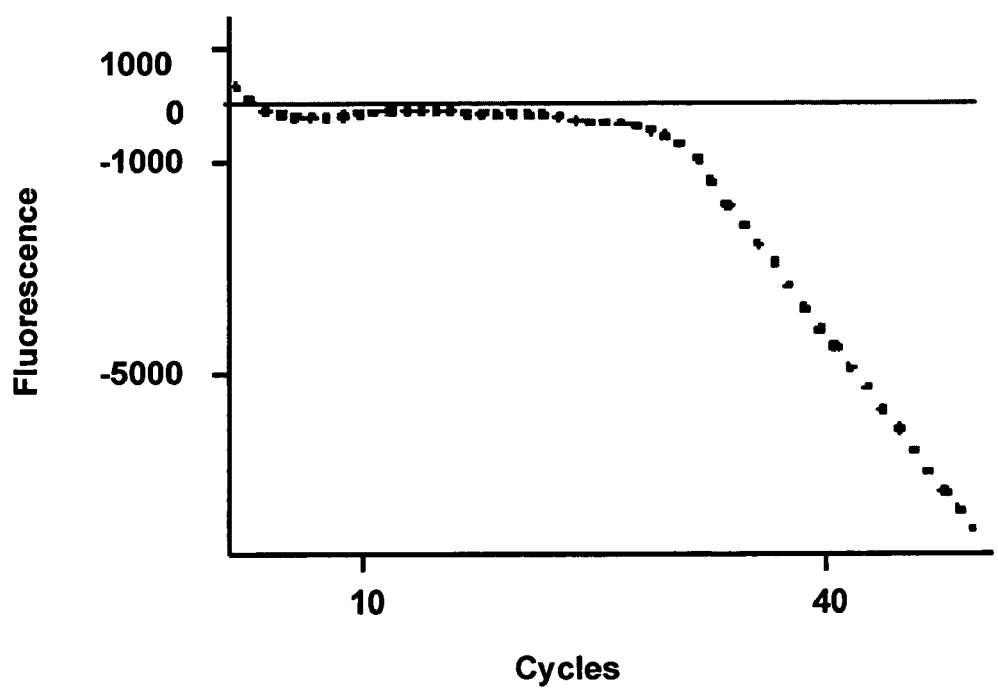
FIG. 16 depicts a self-quenching DDS probe for real-time detection of a single-base HIV-1 drug resistance site. The probe carries an artificial C8 sequence between the fluorescent label and the primer sequence that generates a guanine-rich self-quenching antiprobe segment in the opposite strand. Thus, the signal goes down with target amplification. See Example 10.

This example is based on inserting a string of C bases into the primer/probe at a location immediately adjacent to the 5' fluorescent label (FAM), whereupon target amplification will create an artificial string of G bases in the amplified product that thereby comprises a quencher antiprobe appended to the target segment. In this example, the template consisted of mixed amplicons of the RT gene of HIV-1 wherein 10% of the products contain a common drug resistant mutant at AA position 103 (K103N). This sample thus mimics a patient sample with a 10% 103N resistant subpopulation. The fluor-labeled self-quenching primer/probe employed (SEQ ID NO: 84) is a reverse primer specific to the 103N mutant and contains a hopover modification (GG at 3' end) while the forward primer employs a sequence (SEQ ID NO: 79) that is common to the wild and mutant templates. As seen in FIG. 16 signaling descends rapidly during exponential target amplification as the self-quenching primer/probes are incorporated in the products made. Self-quenching is a product of generating an artificial string of G-bases that are adjacent to the fluor-label of the primer/probe. Thermal cycling conditions employed were: 95 degrees 12 min to initiate hot-start TaqGold polymerase, followed by 50 PCR cycles at 95 degrees 15 sec, 61 degrees 20 sec, and 69 degrees 60 sec.

Example 11

Starved C8 Primer/Probes to Create Roller-Coaster Curves

Figure 17:
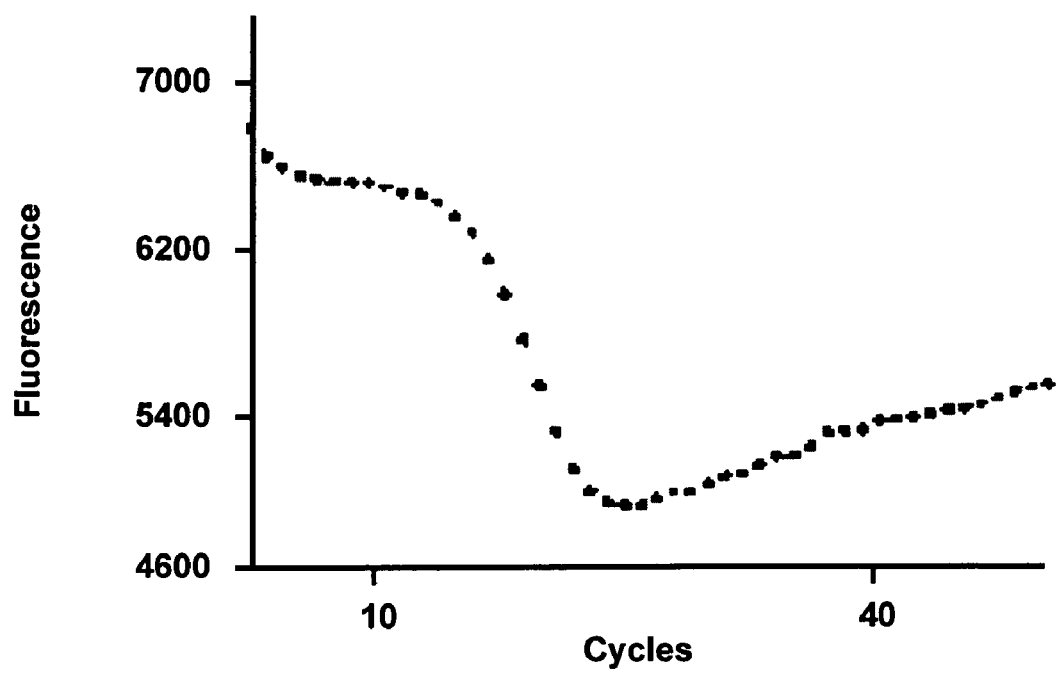
FIG. 17 depicts a "roller-coaster" curve generated by using self-quenching DDS probes applied in a starved concentration of 20 nm so that it runs out during PCR cycling. The curve thus descends till the primer/probe is exhausted, and then reascends as prior products are denatured. The resulting nadir position in these unique curves provides a true quantitative indicator of the number of product amplified. See Example 11.

In this example, a FAM-labeled self-quenching primer/probe (SEQ ID NO: 56) is employed to detect the mutant SNP site of AA378 of the human IL-12 gene (see Example 9 above). However, in this case the primer/probe is provided at a highly reduced concentration of 20 nM, compared to a typical concentration of about 200 nM, so that it runs out during thermal cycling. To avoid asymmetrical amplification, the matching primer (SEQ ID NO: 55) is also provided at a reduced concentration of 25 nM. This example, illustrated by the curve of FIG. 17, is based on thermal cycling conditions similar to the prior example (initial hot-start at 95 degrees 12 min, then 50 PCR cycles at 95 degrees 15 sec, 62 degrees 20 sec, 69 degrees 60 sec).

Since thermal cycling continues after the point where the starved primer/probe is exhausted, further cycling degrades the products made previously, thereby releasing the incorporated primer/probes from close contact with the generated G-string quencher in the matching strand and allowing signal restoration. Thereby, the signal rapidly descends during target amplification and then gradually ascends after the primer/probe concentration is exhausted, resulting in a signaling curve with the profile of a Roller-Coaster. The low point or nadir in the Roller-Coaster curve defines the time point when a defined quantity of product has been made, a new quantitative indicator of real-time PCR amplification.

Example 12

Selective Detection of HIV-1 Drug Resistant Mutant Site K103N

Figure 18:
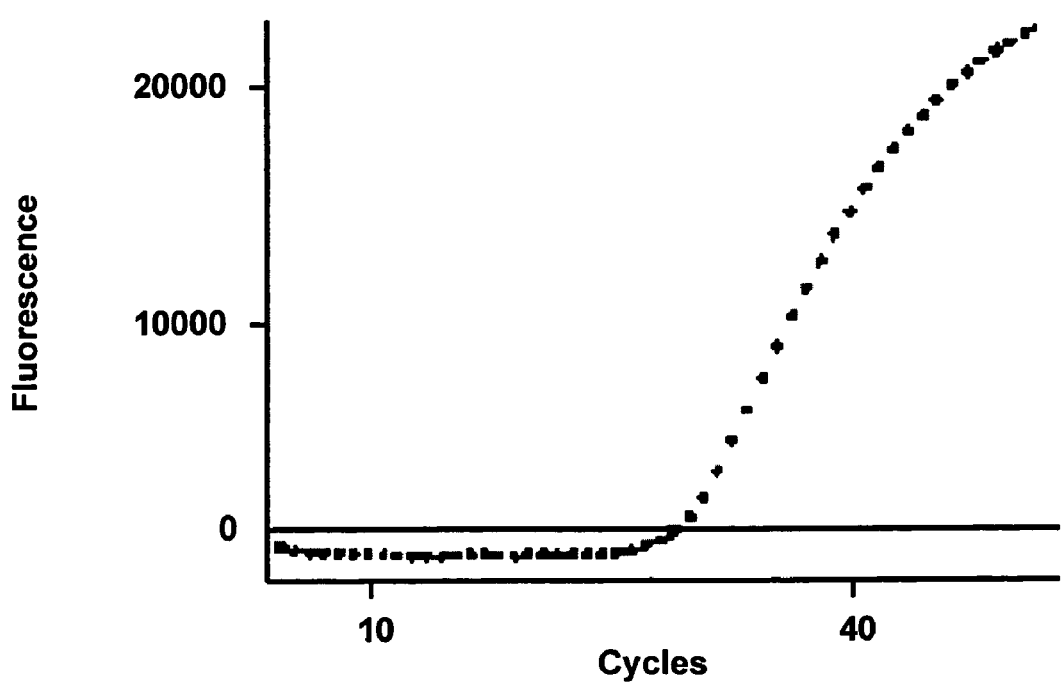
FIG. 18 depicts a real-time amplification curve with a DDS primer/probe for detecting a HIV-1 drug resistance site. See example 12.

This example shows the use of DDS primer/probes to selectively amplify drug resistant mutant sites of HIV-1 by primer extension. The template employed is a RT amplicon of HIV-1 containing the mutant site K103N. Ten thousand copies of the mutant template were provided, and the FAM-labeled primer/probe comprises SEQ ID NO: 80, the BHQ1-labeled antiprobe comprises SEQ ID NO: 81, and the opposing primer comprises SEQ ID NO: 82. Thermal cycling conditions were at: initial hot-start at 95 degrees 10 min, then 50 PCR cycles at 95 degrees 15 sec, 55 degrees 24 sec, and 72 degrees 50 sec. FIG. 18 shows exponential signal amplification starting at about 27 cycles, with product amplification slowing after 40 cycles.

Example 13

Quantitative Detection of HIV-1 K103N Resistant Mutants with Inverse DDS Probes

Figure 19A:
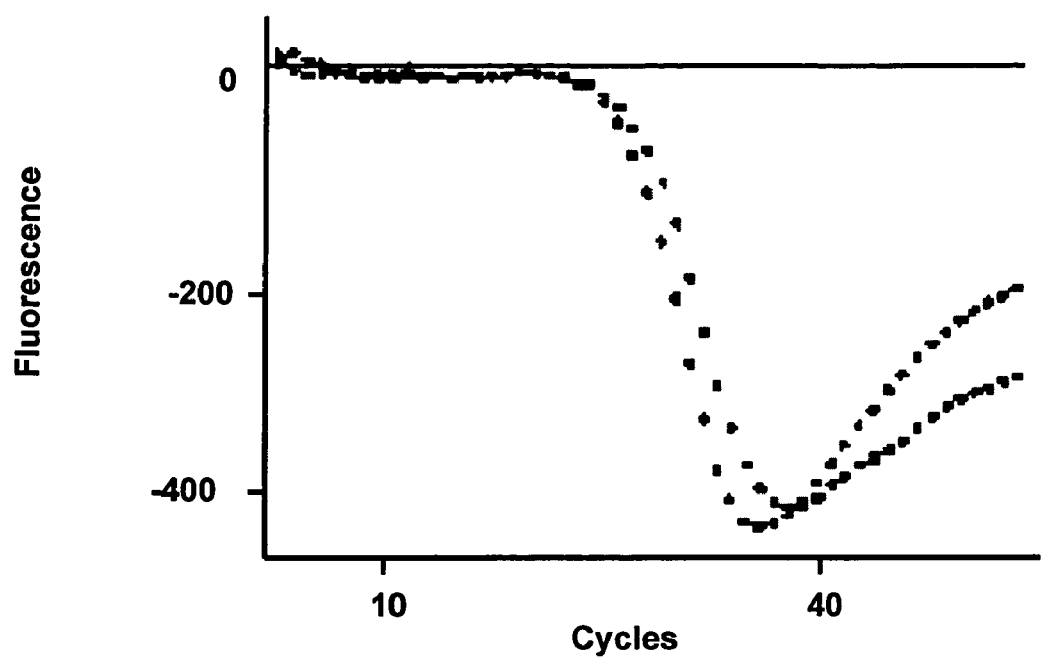
FIGS. 19A-19B depict amplification curves of inverse DDS self-quenching primer/probes to detect the proportion of a specific drug resistant mutant variant vs. Wild type in a HIV-1 sample.
Figure 19B:
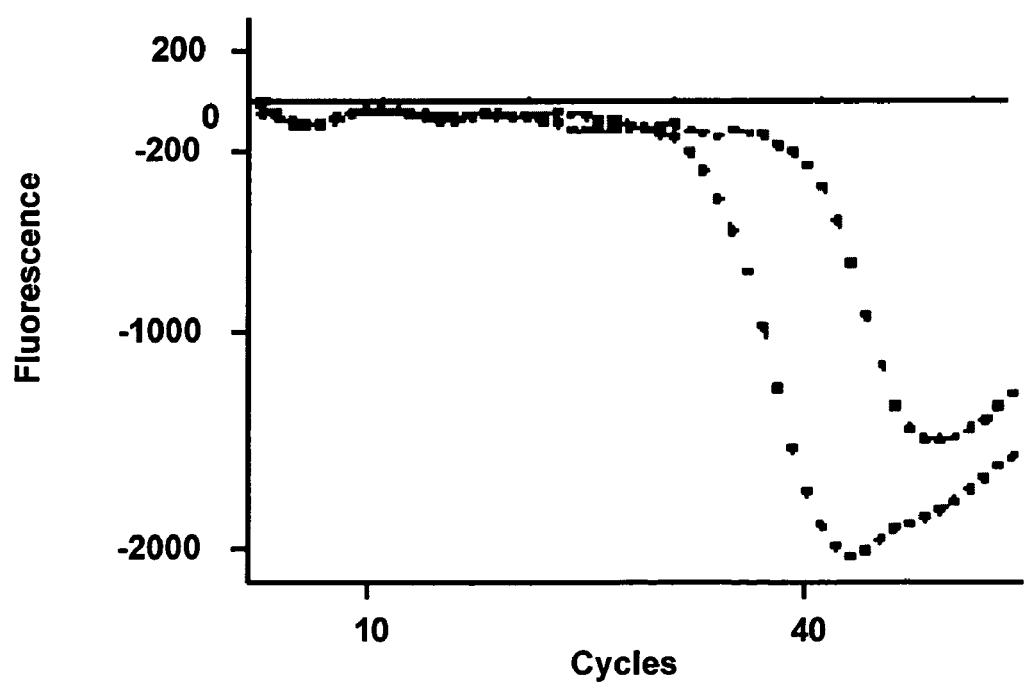

This example illustrates the use of Inverse DDS self-quenching primer/probes at a starved concentration to facilitate quantification of the percent mutant virus in a test sample when low frequencies of the mutant are present. The curves of FIGS. 19A and 19B show discrimination between samples that were mixed with different proportions of wild and mutant template. The curves illustrated compare results from templates mixed with 96% wild/4% mutant (round dark markers) vs. 99.5% wild/0.5% mutant (square gray markers). In these experiments, self-quenching reverse primer/probes for 103K and 103N were provided at a 20 nM concentration and comprise respectively, SEQ ID NO: 57 and 84. A common forward primer (SEQ ID NO: 82) was provided at 25 nM concentration. Thermal cycling conditions were: hot-start at 95 degrees 12 min, then 50 PCR cycles at 95 degrees 15 sec, 61 degrees 24 sec, and 69 degrees 50 sec. FIG. 19A shows nearly parallel curves in detecting the wild template since proportionally, 96% and 99.5% are not too different. In contrast, FIG. 19B shows quite separate curves in detecting the mutant templates which differs substantially in the proportions for 4% mutant vs. 0.5% mutant. Thus, this method provides a means to detect and separate low frequencies of mutant quasispecies.

Example 14

Comparison of Internal DDS Probes or DDS Primer/Probes Vs. Taqman Probes for Real-Time PCR In this example, real-time DDS probes and antiprobes were designed that bind to an internal segment of the target amplicon, between two standard unlabeled primers, in the same manner as standard Taqman probes or molecular beacons are flanked by unlabeled primers. The target template was the HA segment of an H5N1 strain of avian influenza A (Vietnam/Hanoi 30408/2005) with the primers flanking a small upstream site. In this test, the Internal DDS probe and antiprobe (SEQ ID NO: 58, 59) at 23 and 20 bp are both much shorter than the standard Taqman probe (SEQ ID NO: 60) of 31 bp which was employed as a comparison. Shorter probes generally provide greater specificity.

The Taqman probe and primers were modeled after test components described in Ng et al. (Emerging Infectious Diseases, Vol. 11, No. 8, August 2005). The Taqman probe was made with 5' FAM-labeling and 3' quencher-labeling (BHQ1). The DDS probe was 5' FAM-labeled, and the DDS antiprobe was 3' quencher-labeled (BHQ1). A regular DDS primer/probe was also designed and tested, against the same Taqman probe and primer set, using the same sequences (SEQ ID NO: 58, 59) as the Internal DDS probe and antiprobe and thus it binds to the same target site. The difference between the Internal DDS probe and the DDS primer/probe was that the Internal DDS probe was made with an amino on the 3' end to block 3' extension. For this comparison, the Internal DDS probe and antiprobe were provided at 150 nM and 300 nM, comparable to the Taqman probe concentration of 150 nM. However, the DDS primer/probe was provided at 300 nM since it served as a primer. Thermal cycling conditions were: initial hot-start at 95 degrees 10 min, followed by 50 PCR cycles at 95 degrees 15 sec, 58 degrees 45 sec, and 72 degrees 45 sec.

Figure 20:
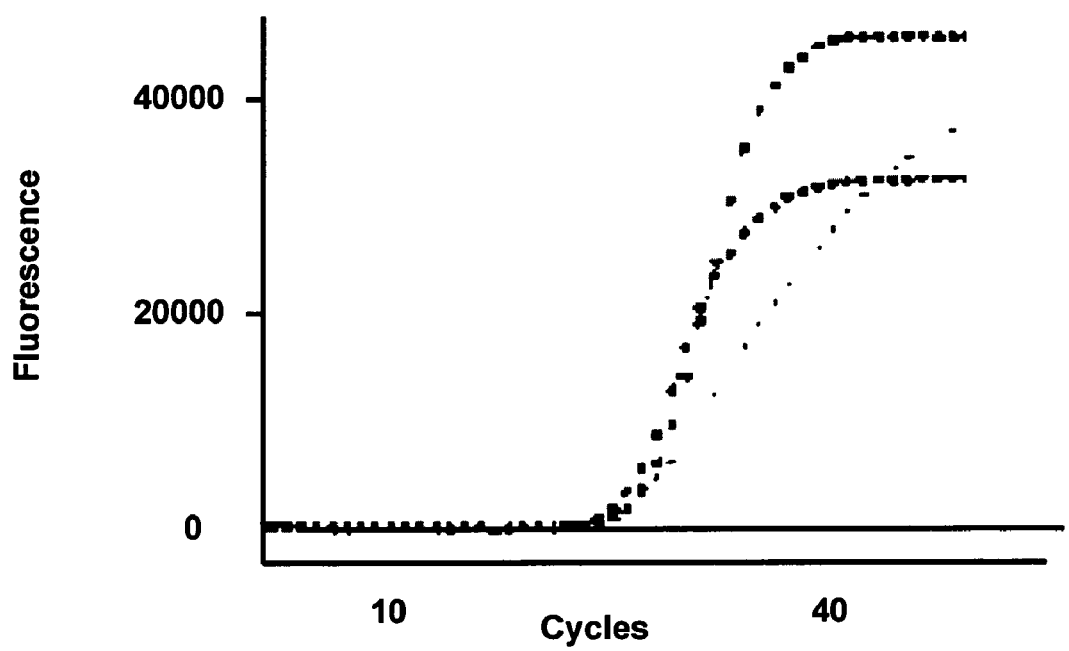
FIG. 20 depict real-time curves comparing the use of Taqman probes vs. Internal DDS probes vs. DDS primer/probes for the same target site in an H5 avian flu sample. The figure compares these three probe types for an upstream H5 target, showing that the DDS probes provide higher signaling. See Example 14.

FIG. 20 depicts three curves based on these probes for the same target site, wherein the Taqman probe is indicated by dark round dots, the DDS primer/probe is indicated by dark squares, and the Internal DDS probe is indicated by gray triangles. The Taqman and the Internal DDS probes employed the same unlabeled forward primer (SEQ ID NO: 61). As can be seen, all three curves start exponential amplification at about the same time, however the curve for the DDS probe follows the same slope and signaling ascends considerably higher (about 40%) vs. the Taqman probe, while the Internal DDS probe follows a more graduated slope and ascends about 18% higher than the Taqman probe. Although this finding suggests that Internal DDS probes are not highly advantaged over Taqman probes in sensitivity, they still provide a major improvement in specificity. Examination of the raw curves (without normalizing the curves to a zero baseline) reveal that the Taqman curves start signaling at a high baseline level (about 24000) compared to the DDS-based curves which start at a lower level (about 6000), and both go up to about the same maximum level (about 54000 for Taqman, and about 57000 for DDS) and this probably explains the greater signaling potential of the DDS-based probes. With a DDS probe and antiprobe pair, the fluor-labeled and the quencher-labeled ends of these components are brought adjacent to one another and remain so, while with Taqman probes, the fluor-end and the quencher-end are only in proximity on a statistical basis, depending on when each probe molecule is in a folded/coiled configuration vs. a more extended configuration. Therefore, the baseline for Taqman signaling runs high, and thus its signaling potential from that point is significantly reduced compared to DDS-based probes.

Example 15

Stringent Detection with Hopover Modified Primer/Probes

Figure 21:
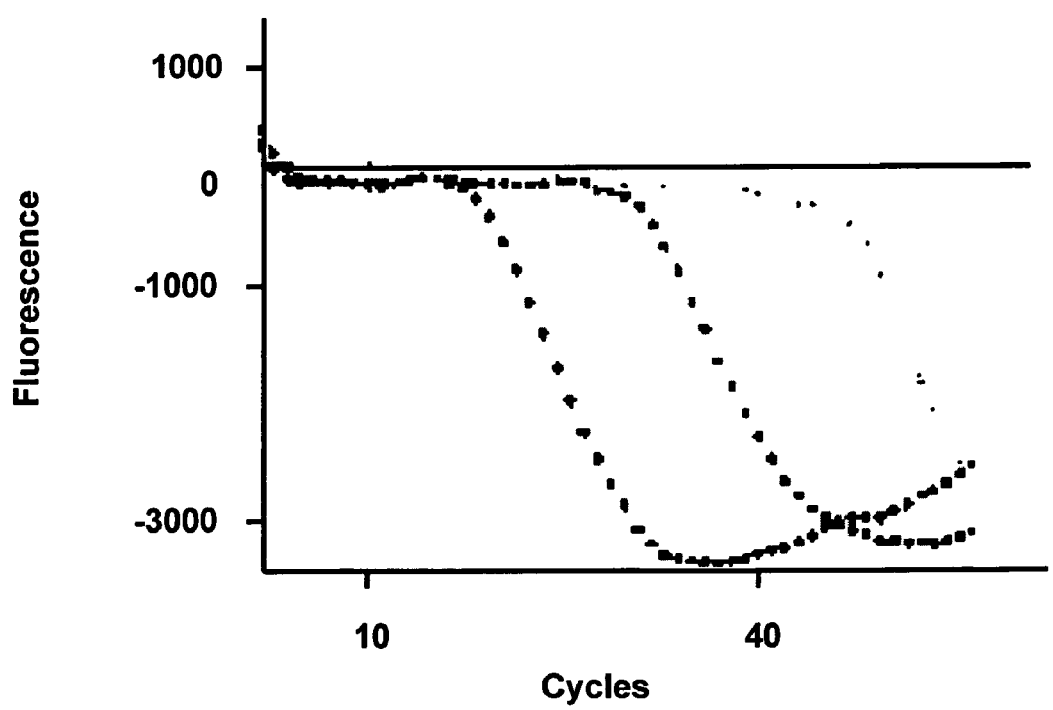
FIG. 21 depicts the effect of providing inverse DDS primer/probes that are mismatched in one or more bases adjacent to the 3' end in order to increase specificity. The rightward shift in the curves indicates that this "hopover" modification comes at a cost of reduced sensitivity. See Example 15.

This example shows the use of primer/probes where the base or bases immediately adjacent to the 3' mutant specific primer base is modified to increase specificity. In this case, FAM-labeled self-quenching primer/probes are employed and the probes are modified with one or two G substitutions for one or two T bases that should be in one or two penultimate positions of the probe. The probes thus comprise SEQ ID NO: 83, 84, and 64. (103N probes with -TTG, -TGG, -GGG at their 3' ends). As can be seen in FIG. 21, hopover modified probes restrict and delay the amplification of their respective products, perhaps too much in the case of using 2 base substitutions. Similar but somewhat different stringency can be achieved by increasing the annealing temperature. The thermal cycling conditions employed were: hot-start at 95 degrees 12 min, then 55 PCR cycles at 95 degrees 15 sec, 61 degrees 24 sec, and 69 degrees 50 sec.

Example 16

Detecting RSV Strains with Two Color or Two Label DDS Primer/Probes

Figure 22:
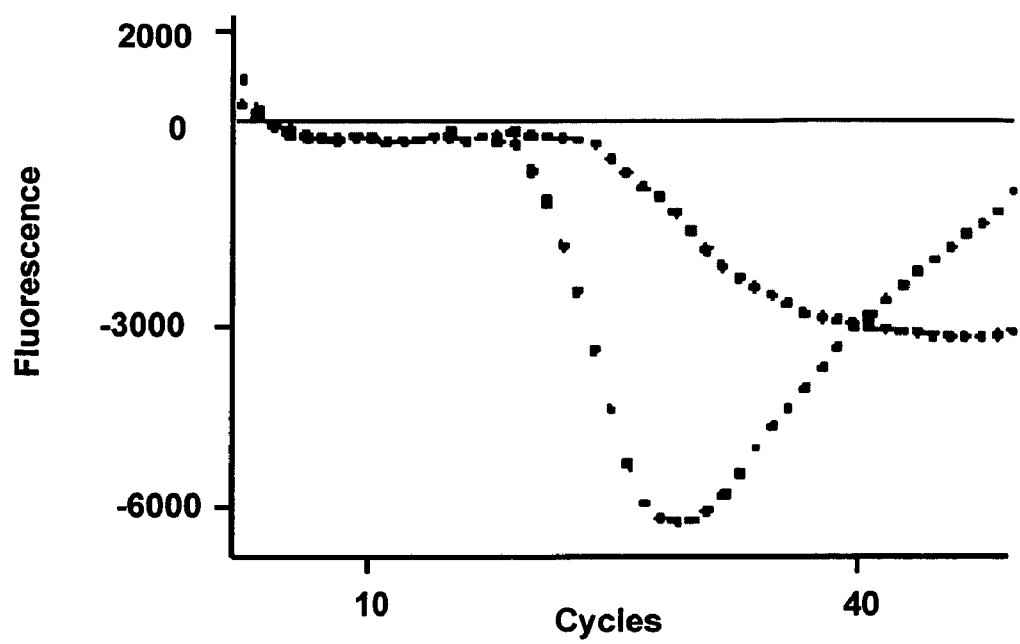
FIG. 22 depicts curves produced by using labeled primer/probes on both ends (curve marked with dark squares) to provide double signaling as well as greater sensitivity. See Example 16.

In this example, the primer/probes were provided with single or double labeling. FIG. 22 shows curves indicating the detection of RSV strain A2 using either one or two Inverse DDS primer/probes. Double detection employed both a FAM-labeled self-quenching primer/probe (SEQ ID NO: 68) for the reverse primer position (dark round dots), and a second FAM-labeled self-quenching primer/probe (SEQ ID NO: 69) for the forward primer position (gray squares). Clearly, the use of paired FAM labeled primer/probes provides a stronger signaling change as well as earlier detection compared to using one labeled primer/probe.

Example 17

Universal DDS Probes to Detect Multiple Sites Separately or in Combination

Figure 23:
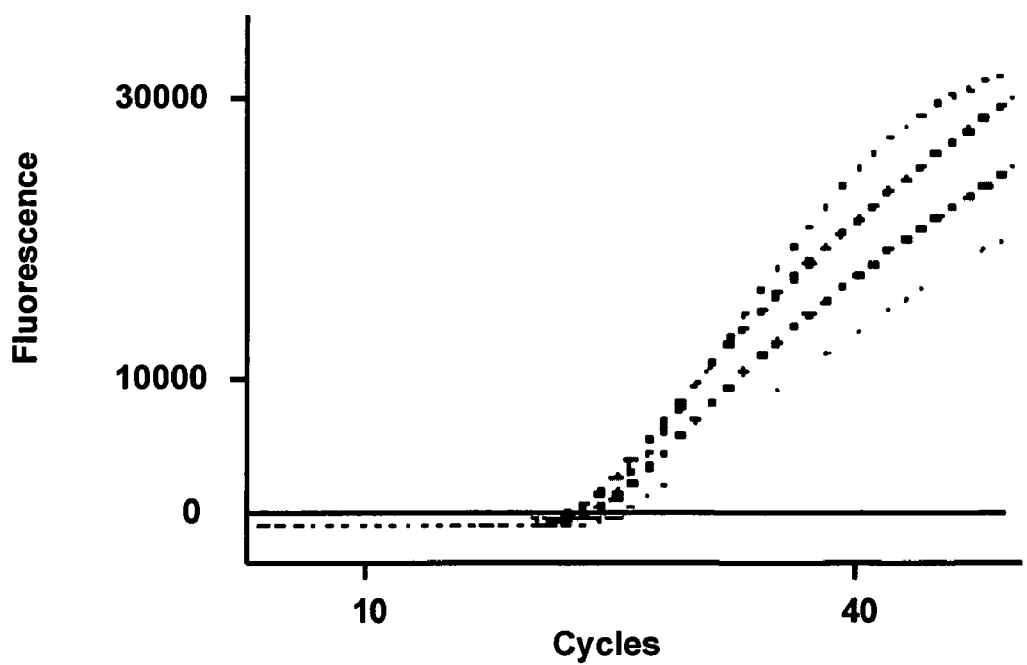
FIG. 23 depicts multiplex detection of three H5 avian flu sites based upon using a common universal DDS primer/probe and antiprobe in combination with site-specific linker/primers that carry a common 5' universal linker. Each probe set was run separately or all together (gray diamonds). See Example 17.

This example illustrates the use of universal probes and antiprobes to detect different target sites with the same basic signaling components. Here an H5N1 avian flu strain (Vietnam/Hanoi 30408/2005) is detected at three different sites in the HA gene region using a common FAM-labeled universal probe (SEQ ID NO: 1) and BHQ1-labeled universal antiprobe (SEQ ID NO: 85). Four tests were run for this series, with three individual tests showing each target site detected separately, and with one joint test showing all three sites in combination. All tests employed the same universal probe and antiprobe, and these universal components were added in high concentration at the same time as the primers specific to each target. The three target sites are initially amplified with three different target-specific primer pairs consisting of a primer with a universal linker attached and an opposing primer. These primer pairs targeted: 1) a upstream segment of the gene (SEQ ID NO: 70 and 71), 2) a mid-section of the gene (SEQ ID NO: 72 and 73), and 3) a downstream segment of the gene (SEQ ID NO: 74 and 75). Each linker primer is provided at a low concentration (10 nM), and each opposing primer is provided at a high concentration (200 nM). The longer universal probe takes over amplification by preferentially binding to the appended universal linker site. The universal antiprobe quenches unused universal probes. FIG. 23 illustrates these four tests, showing three curves indicating detection and amplification of the three H5 sites separately: 1) upstream segment (dark round dots), 2) mid segment (dark gray squares) and 3) downstream segment (light gray triangles), and a fourth curve (light diamonds) showing multiplex amplification and detection of all three H5 sites together using the same universal primer/probe. These results indicate sensitive and specific H5 detection. For each separate test, the universal probe is provided at 200 nM and the universal antiprobe is provided at 400 nM. For the combination test, the concentrations of the universal probe and antiprobe are increased to 300 nM and 600 nM, respectively. Thermal cycling conditions employed were: hot-start at 95 degrees 10 min, then 50 PCR cycles at 95 degrees 15 sec, 58 degrees 45 sec, and 72 degrees 45 sec.

Example 18

Real Time Detection with Reverse-Labeled DDS Primer/Probes

Figure 24:
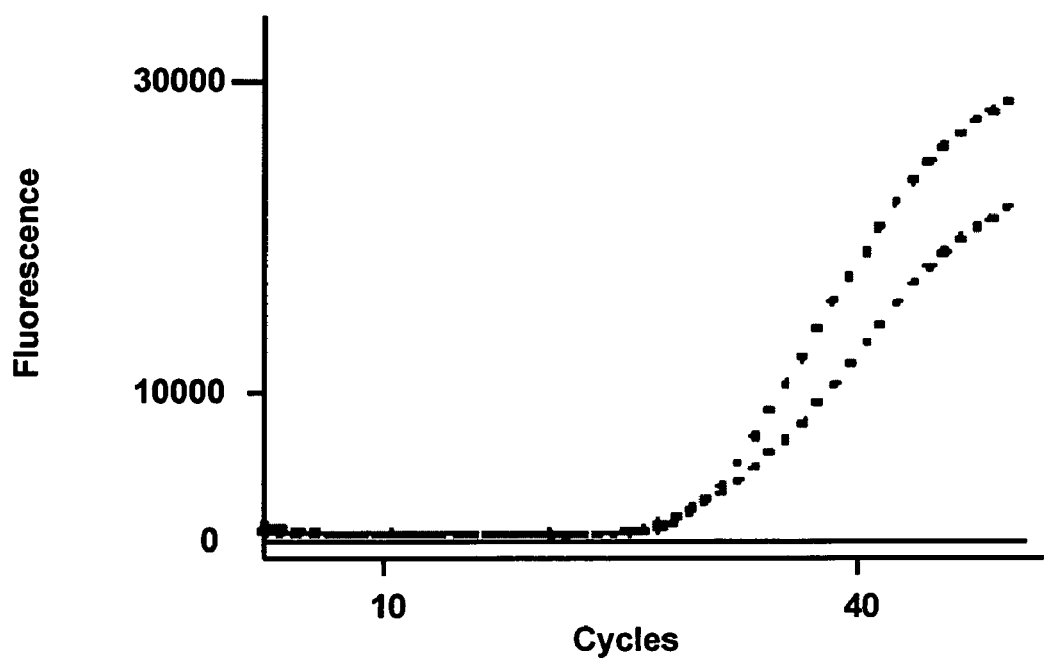
FIG. 24 depicts real-time detection with a reverse-labeled DDS primer/probe vs. A universal DDS probe, both for the same H5 avian flu target site. See Example 18.
Figure 25:
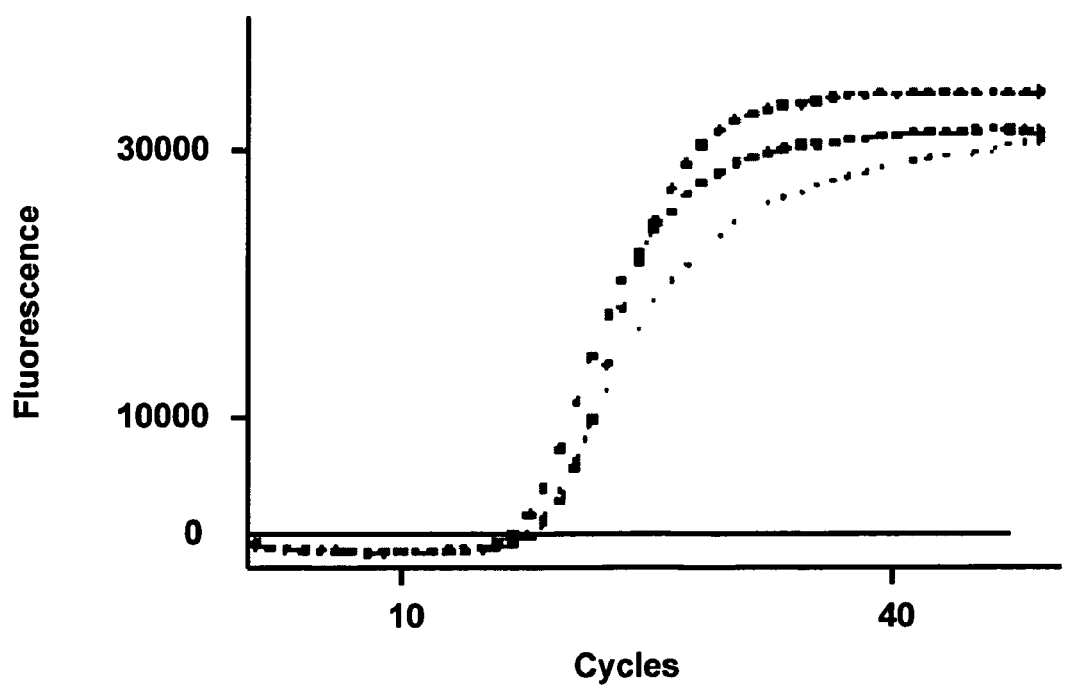
FIG. 25 depicts curves of real-time PCR with a Taqman probe for H5N1 flu, the Hong Kong strain, but tested with that strain and two closely related strains identified as Vietnam and Hanoi which differ from Hong Kong by two or three bases in the probe region. All curves are similar and do not differentiate the strain variation.
Figure 26:
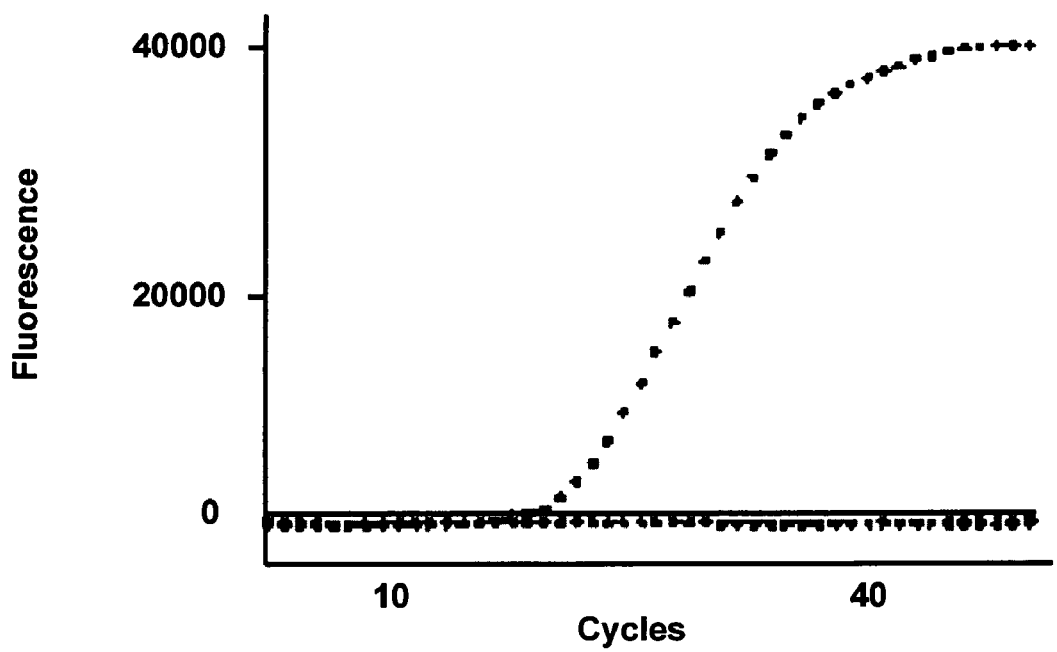
FIG. 26 depicts real-time PCR curves with an Internal DDS probe for H5N1 flu that is also specific to the Hong Kong sequence vs. the Vietnam and Hanoi sequence in the same target region as described for the Taqman probe test shown above. The DDS probe correctly detects only the Hong Kong strain.
Figure 27:
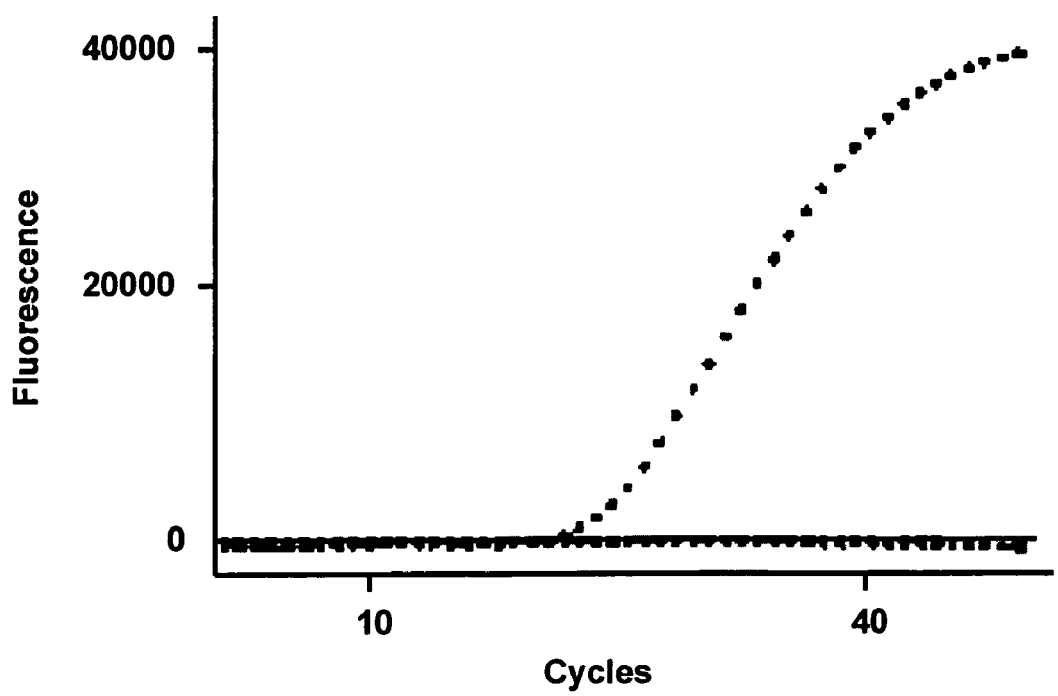
FIG. 27 depicts the same test as above, but with the annealing temp lowered to 42 degrees. The Internal DDS probe still only detects the correct target.
Figure 28:
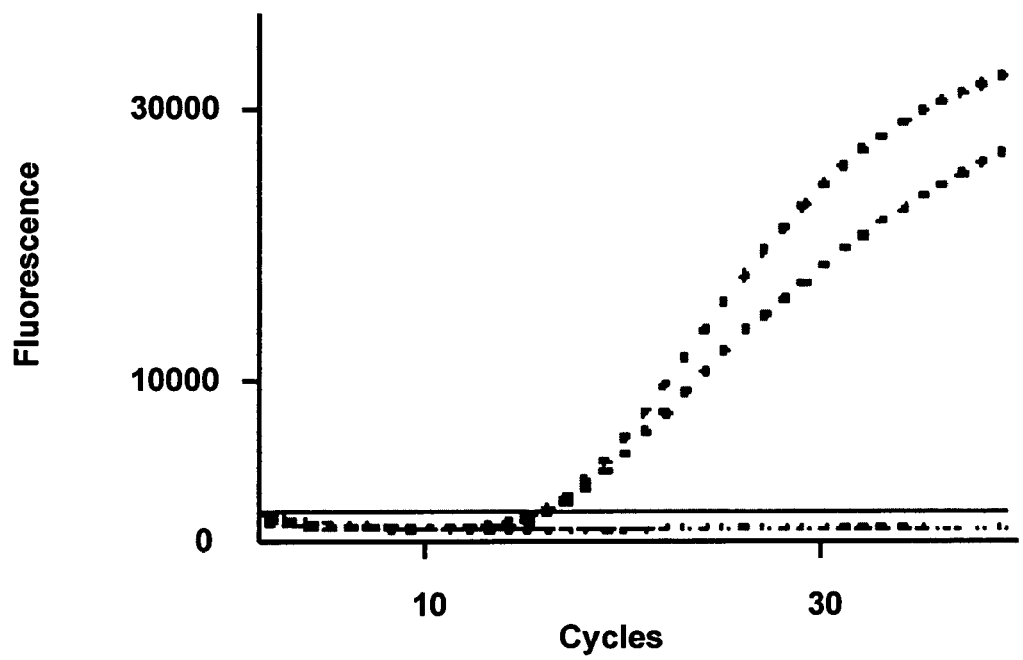
FIG. 28 depicts curves from Internal DDS probes that are specific to a 16s target site that differs between MTB and *M. avium* (paratuberculosis) by one base. The MTB specific probe detects only the MTB template and the avium specific probe detects only the avium template. This single base differentiation was achieved with an annealing temp of 58 degrees.
Figure 29:
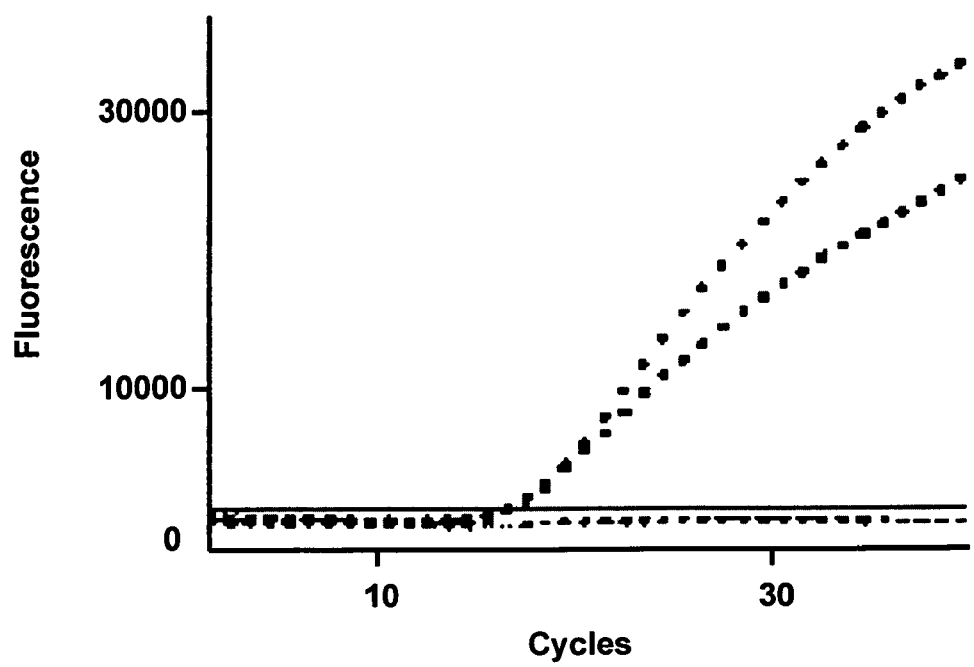
FIG. 29 depicts similar curves to FIG. 28 showing the same single base differentiation, but with the annealing temp lowered to 35 degrees.
Figure 30:
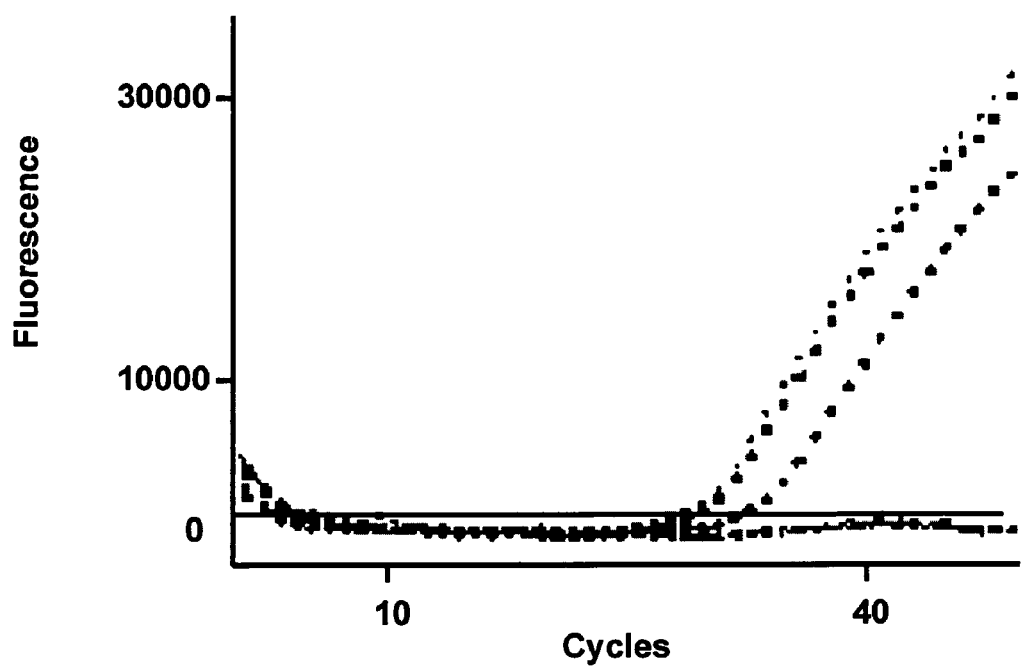
FIG. 30 depicts selective single base discrimination of a drug resistant mutant site of HIV-1 using Internal DDS probes for either 103N, a resistant mutant, and 103K, the wild type. The 103K and 103N specific probes only detect the correct matching template.
Figure 31:
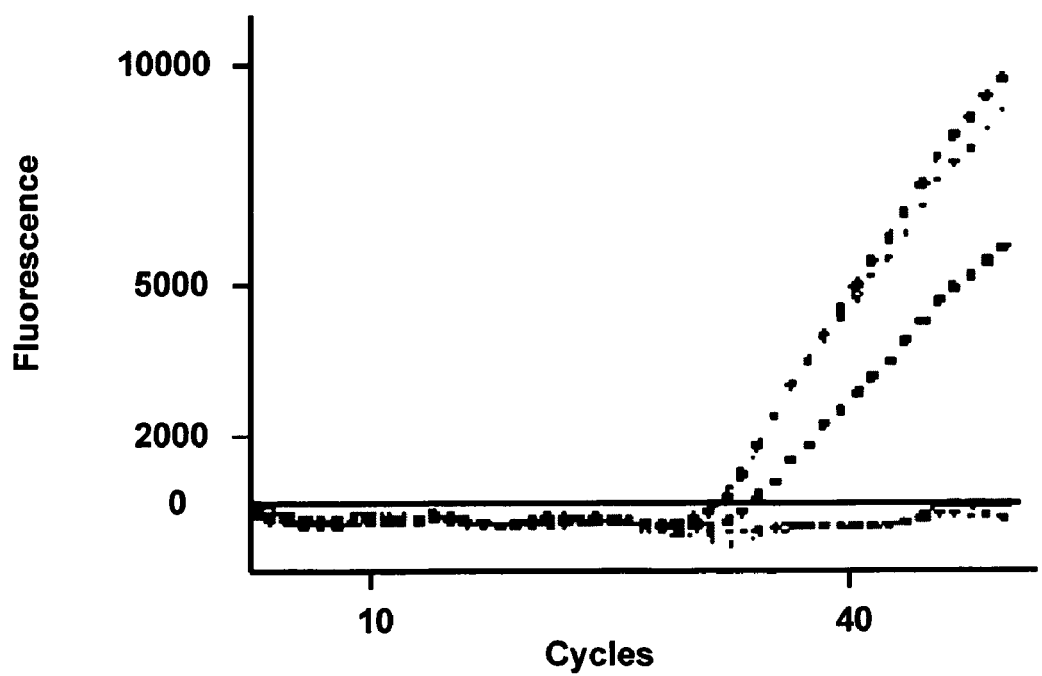
FIG. 31 depicts curves similar to FIG. 30 using the same probes and templates but lowering the annealing temp to 25 degrees. The DDS probes continue to detect only the correct sequence even at this low, highly permissive temperature.

This example illustrates reverse-labeling of DDS probes for detection of the same H5 mid-section target used in Example 17. In this case, the primer/probe (SEQ ID NO: 76) is labeled on the 5' end with a quencher compound, and the antiprobe (SEQ ID NO: 77) is 3' labeled with FAM. Both reagents are provided at a concentration of 200 nM. Incorporation of the quencher-labeled probes into target products will displace fluorescent-labeled antiprobes, releasing their signaling potential. Thus, signaling rises with exponential target amplification. This reverse-labeled DDS curve is marked by dark squares in FIG. 24.

The second comparative curve, marked by dark round dots, targets the same H5 mid-section sequences using a linker/primer (SEQ ID NO: 72) of Example 17 at 10 nM concentration that automatically transitions to a universal probe and antiprobe (SEQ ID NO: 1, 85) provided at 200 and 400 nM, respectively. Both products employ the same unlabeled reverse primer (SEQ ID NO: 73) at 200 nM. Cycling conditions were the same as Example 17. Both submethods show exponential amplification starting at about the same time although the slopes of the curves are somewhat different.

Similar to this example, many other probe-antiprobe labeling variations have been tested with a fluorescent donor label paired with an acceptor moiety comprising either a quencher compound, a longer wavelength fluorescent compound or an artificial guanine-rich segment appended to the probe or antiprobe that serves as a quencher. With these variations, detection sensitivity depends on the specific labeling pairs utilized. The other labeling variations thus far found useful for real-time PCR detection are: 5' donor-labeled probe (FAM) with a 3' acceptor-labeled antiprobe (Cy3); 5' acceptor-labeled probe (HEX) with a 3' donor-labeled antiprobe (FAM); 3' donor-labeled probe (FAM) with a 5' acceptor-labeled antiprobe (BHQ1 or Iowa Black); 5' donor-labeled probe (HEX) with a 3' acceptor labeled antiprobe (6 guanines); 5' and 3' donor labeled probe (Cy3) with a 3' and 5' acceptor labeled antiprobe (Iowa Black), a unimolecular probe-antiprobe polynucleotide with a 5' donor labeled probe end (FAM) and a 3' acceptor labeled antiprobe end (BHQ1).

Example 19

Real Time PCR Detection of Single Base Differences with Internal DDS Probes

This example illustrates the high specificity of the Internal DDS probe system for discriminating important pathogens. The first test employed an internal DDS probe for H5 flu targeting the same site used in Example 14. Three strains of H5 were tested with both a Taqman probe and a Internal DDS probe, with both probe sequences based on the Hong Kong strain, and with test samples including the Vietnam and Hanoi strains which differ by 2 or 3 bases in the probe sequence. With standard annealing temperatures in the range of 58 to 62 degrees, the Taqman probe did not differentiate the three strains but the DDS probe only detected the Hong Kong strain. Further studies showed that the DDS probe continued to show exact strain differentiation even with annealing temperatures lowered to 42 degrees. See FIGS. 25-27. A similar test was done with Internal DDS probes for the 16s gene of MTB and *M. avium*, at a site containing only one base difference. The DDS probes and antiprobes of SEQ ID NO. 17 to 20 only detected the correct template with MTB or avium specific probes even when the annealing temperature was lowered to 35 degrees (FIGS. 28-29). Indeed, similar probes for four nearby sites were tested and proved effective for single base discrimination and a fifth nearby site was tested with paired probes and antiprobes of SEQ ID NO. 21 to 24 where the templates and probes comprise four bases that are different. All such tests gave clear discrimination.

Finally, tests were run with an HIV-1 drug resistant site 103N as the target versus the wild type site 103K which differs by one base, G vs. T, that confers resistance to standard HIV drugs. Internal DDS probes were made for both 103N and 103K detection (SEQ ID NO 25 to 28) and when run against 3 different samples including two mutants, all determinations were correct. This remarkable specificity continued even when the annealing temp was brought down to 25 degrees, room temperature—a fail safe procedure (FIGS. 30-31).

Any publications or patents mentioned in this specification are indicative of the levels of those skilled in the art to which the invention pertains. Further, these publications are incorporated by reference herein to the same extent as if each individual publication was specifically and individually incorporated by reference. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:

1. A universal probe-antiprobe composition to detect a target nucleotide sequence in a sample, the composition comprising:
(a) a universal linker/primer comprising
(i) a 5' universal linker sequence, wherein the 5' universal linker sequence is not complementary to any sequence in the sample; and
(ii) a 3' primer sequence complementary to the target nucleotide sequence;
(b) a universal probe comprising
(i) a universal primer sequence that substantially corresponds to the universal linker sequence of the universal linker/primer; and
(ii) a first labeling component; and
(c) a universal antiprobe comprising
(i) a sequence complementary to a partial sequence of the universal probe; and
(ii) a second labeling component; the composition suitable for real-time amplification and detection of a specific target sequence.

2. The universal probe-antiprobe composition of claim 1, comprising a universal primer sequence that is not complementary to any sequence in a natural organism.

3. The universal probe-antiprobe composition of claim 1, wherein the universal probe is a self-quenching universal probe comprising sequentially: (i) a 5' fluorescent labeling compound; (ii) a cytidine-rich sequence comprising about 2 to about 8 cytidines; and (iii) a 3' universal primer sequence; and wherein the composition does not comprise a universal antiprobe.

4. The universal probe-antiprobe composition of claim 1, wherein the composition comprises a common universal probe and antiprobe and two or more universal linker/primers; wherein the two or more universal linker/primers comprise different primer sequences specific to different target sites and a common universal linker sequence; wherein the common universal probe produces a combined detection signal to avoid false a negative in a multiplex amplification of different targets.

5. The universal probe-antiprobe composition of claim 1, wherein the composition comprises two or more different universal probes and anti probes and two or more universal linker/primers; wherein the two or more universal linker/primers comprise different primer sequences specific to different target sites and different universal linkers specific to the different universal probes and antiprobes; comprising different labeling components effective to produce a pattern of two or more signals that confirm detection to avoid a false positive in a multiplex amplification of different targets.

6. The universal probe-antiprobe composition of claim 1, wherein false negative or false positive tests are avoided by (i) employing a common self-quenching universal probe with two or more universal linker/primers that prime, amplify and label different targets with the same signal; or by (ii) employing two or more self-quenching universal probes and universal linker/primers that prime, amplify and label different targets with different signals.

7. The universal probe-antiprobe composition of claim 1, wherein the universal primer/probe comprises a sequence comprising one of SEQ ID NOS:1 to 16.

8. The composition of claim 1, wherein the composition exhibits a first signaling state when the first and second labeling components are in proximity due to binding of the universal probe and the universal anti probe, and a second signaling state when the first and second labeling components are dissociated due to binding of the universal probe to the target nucleotide sequence, and wherein the first signaling state switches to the second signaling state relative to the presence and frequency of the target nucleotide sequence in the sample.

9. The composition of claim 8, wherein the first and second labeling components comprise a FRET donor-acceptor pair that is a fluorescent donor compound paired with a fluorescent acceptor moiety, wherein the fluorescent acceptor moiety comprises either a longer wavelength fluorescent compound, a quencher compound, or a guanine-rich sequence segment having about 2 to about 8 guanines; wherein the signaling state of the composition is modulated by the proximity of the donor and acceptor labeling components.

10. The composition of claim 8, wherein the first and second labeling components are selected from the group consisting of a FRET donor-acceptor pair, FAM, TET, HEX, JOE, VIC, ROX, NED, Texas Red, Yakima Yellow, BHQI, BHQ2, BHQ3, Iowa Black FQ, Iowa Black RQ, TAMRA, DABCYL, ElleQuencher, Eclipse Dark Quencher, Methyl Red, DisperseBlue3, Bodipy 493/503, the Cy dyes Cy2, Cy3, Cy3.5, Cy5, Cy5.5, and Cy7, the AlexaFluor dyes 488, 532, 546, 555, 568, 594, 610, 647, and 680, the PromoFluor dyes 488, 555, 590, 633, 647, and 680, a fluorescent compound, a quencher compound, a color dye compound, a quantum dot, a silver or nanogold compound, and a guanine-rich sequence segment.

11. The composition of claim 10, wherein the first and second labeling components are a FRET donor-acceptor pair.

12. The composition of claim 11, wherein the labeling configuration of the FRET donor acceptor pair is selected from the group consisting of a 5' donor-labeled probe and a 3' acceptor-labeled antiprobe; a 3' donor-labeled probe and a 5' acceptor-labeled antiprobe; a 3' acceptor-labeled probe and a 5' donor-labeled antiprobe; a 5' acceptor-labeled probe and a 3' donor-labeled antiprobe; a 5' and 3' donor-labeled probe and a 5' and 3' acceptor-labeled antiprobe; a 5' and 3' acceptor-labeled probe and a 5' and 3' donor-labeled antiprobe; a probe with 5' donor-label and 3' acceptor-label and an antiprobe with 3' acceptor-label and 5' donor-label; a probe with 5' acceptor-label and 3' donor-label and an antiprobe with 3' donor-label and 5' acceptor-label; a probe with a central donor-label and an antiprobe with a central acceptor-label; and a probe with a central acceptor-label and an antiprobe with central donor-label.

* * * * *

SEQUENCE LISTING

```
<160> NUMBER OF SEQ ID NOS: 85

<210> SEQ ID NO 1
<211> LENGTH: 27
<212> TYPE: DNA
<213> ORGANISM: artificial sequence
<220> FEATURE:
<223> OTHER INFORMATION: universal probe with 5' fluorescent label

<400> SEQUENCE: 1
ccctatcgct acgtagacta gacgttc                                    27
```

```
<210> SEQ ID NO 2
<211> LENGTH: 27
<212> TYPE: DNA
<213> ORGANISM: artificial sequence
<220> FEATURE:
<223> OTHER INFORMATION: universal probe with 5' fluorescent label

<400> SEQUENCE: 2
cctagaccta cgacataggt accctac                                           27

<210> SEQ ID NO 3
<211> LENGTH: 27
<212> TYPE: DNA
<213> ORGANISM: artificial sequence
<220> FEATURE:
<223> OTHER INFORMATION: universal probe with 5' fluorescent label

<400> SEQUENCE: 3
ctacaatacg ttaacgccta agagtag                                           27

<210> SEQ ID NO 4
<211> LENGTH: 27
<212> TYPE: DNA
<213> ORGANISM: artificial sequence
<220> FEATURE:
<223> OTHER INFORMATION: universal probe with 5' fluorescent label

<400> SEQUENCE: 4
catagaacta gcacgctacg tactagg                                           27

<210> SEQ ID NO 5
<211> LENGTH: 29
<212> TYPE: DNA
<213> ORGANISM: artificial sequence
<220> FEATURE:
<223> OTHER INFORMATION: universal probe with 5' fluorescent label

<400> SEQUENCE: 5
ccccccctct cccttcttcg aacttactc                                         29

<210> SEQ ID NO 6
<211> LENGTH: 29
<212> TYPE: DNA
<213> ORGANISM: artificial sequence
<220> FEATURE:
<223> OTHER INFORMATION: universal probe with 5' fluorescent label

<400> SEQUENCE: 6
ccccccctcc tacgacatag gtaccctac                                         29

<210> SEQ ID NO 7
<211> LENGTH: 27
<212> TYPE: DNA
<213> ORGANISM: artificial sequence
<220> FEATURE:
<223> OTHER INFORMATION: universal probe with 5' fluorescent label

<400> SEQUENCE: 7
ccctagcgct acgtagacta tttcacg                                           27

<210> SEQ ID NO 8
<211> LENGTH: 27
<212> TYPE: DNA
<213> ORGANISM: artificial sequence
<220> FEATURE:
<223> OTHER INFORMATION: universal probe with 5' fluorescent label
```

```
-continued

<400> SEQUENCE: 8
cccttacgca tcgactaggt agacttc                                27

<210> SEQ ID NO 9
<211> LENGTH: 27
<212> TYPE: DNA
<213> ORGANISM: artificial sequence
<220> FEATURE:
<223> OTHER INFORMATION: universal probe with 5' fluorescent label

<400> SEQUENCE: 9
cccgtagact agacgttccg ctattac                                27

<210> SEQ ID NO 10
<211> LENGTH: 27
<212> TYPE: DNA
<213> ORGANISM: artificial sequence
<220> FEATURE:
<223> OTHER INFORMATION: universal probe with 5' fluorescent label

<400> SEQUENCE: 10
cccgactacg tacgctagac gtatttc                                27

<210> SEQ ID NO 11
<211> LENGTH: 27
<212> TYPE: DNA
<213> ORGANISM: artificial sequence
<220> FEATURE:
<223> OTHER INFORMATION: universal probe with 5' fluorescent label

<400> SEQUENCE: 11
ccctacgtag accgctagtt cacgtat                                27

<210> SEQ ID NO 12
<211> LENGTH: 27
<212> TYPE: DNA
<213> ORGANISM: artificial sequence
<220> FEATURE:
<223> OTHER INFORMATION: universal probe with 5' fluorescent label

<400> SEQUENCE: 12
ccctagacgt tctattacgt agaccgc                                27

<210> SEQ ID NO 13
<211> LENGTH: 27
<212> TYPE: DNA
<213> ORGANISM: artificial sequence
<220> FEATURE:
<223> OTHER INFORMATION: universal probe with 5' fluorescent label

<400> SEQUENCE: 13
cccataatcc tactgatcgc gtgcaag                                27

<210> SEQ ID NO 14
<211> LENGTH: 24
<212> TYPE: DNA
<213> ORGANISM: artificial sequence
<220> FEATURE:
<223> OTHER INFORMATION: universal probe with 5' fluorescent label

<400> SEQUENCE: 14
tacgttaacg cctagcaaga gtaa                                   24
```

```
<210> SEQ ID NO 15
<211> LENGTH: 24
<212> TYPE: DNA
<213> ORGANISM: artificial sequence
<220> FEATURE:
<223> OTHER INFORMATION: universal probe with 5' fluorescent label

<400> SEQUENCE: 15
caattgcgga ttcacgttat gatc                                          24

<210> SEQ ID NO 16
<211> LENGTH: 24
<212> TYPE: DNA
<213> ORGANISM: artificial sequence
<220> FEATURE:
<223> OTHER INFORMATION: universal probe with 5' fluorescent label

<400> SEQUENCE: 16
tagcaagagt aatacgttaa cgcc                                          24

<210> SEQ ID NO 17
<211> LENGTH: 20
<212> TYPE: DNA
<213> ORGANISM: artificial sequence
<220> FEATURE:
<223> OTHER INFORMATION: internal probe with 5' donor and 3' block
      for Mycobacterium tuberculosis

<400> SEQUENCE: 17
catgtcttgt ggtggaaagc                                               20

<210> SEQ ID NO 18
<211> LENGTH: 20
<212> TYPE: DNA
<213> ORGANISM: artificial sequence
<220> FEATURE:
<223> OTHER INFORMATION: internal probe with 5' donor and 3' block
      for Mycobacterium avium

<400> SEQUENCE: 18
catgtcttct ggtggaaagc                                               20

<210> SEQ ID NO 19
<211> LENGTH: 17
<212> TYPE: DNA
<213> ORGANISM: artificial sequence
<220> FEATURE:
<223> OTHER INFORMATION: antiprobe with 3' acceptor for
      Mycobacterium tuberculosis

<400> SEQUENCE: 19
ttccaccaca agacatg                                                  17

<210> SEQ ID NO 20
<211> LENGTH: 17
<212> TYPE: DNA
<213> ORGANISM: artificial sequence
<220> FEATURE:
<223> OTHER INFORMATION: antiprobe with 3' acceptor for
      Mycobacterium avium

<400> SEQUENCE: 20
ttccaccaga agacatg                                                  17

<210> SEQ ID NO 21
<211> LENGTH: 23
<212> TYPE: DNA
<213> ORGANISM: artificial sequence
```

```
<220> FEATURE:
<223> OTHER INFORMATION: internal probe with 5' donor and 3'
      block for Mycobacterium tuberculosis

<400> SEQUENCE: 21
taggaccacg ggatgcatgt ctt                                              23

<210> SEQ ID NO 22
<211> LENGTH: 23
<212> TYPE: DNA
<213> ORGANISM: artificial sequence
<220> FEATURE:
<223> OTHER INFORMATION: internal probe with 5' donor and 3'
      block for Mycobacterium avium

<400> SEQUENCE: 22
taggacctca agacgcatgt ctt                                              23

<210> SEQ ID NO 23
<211> LENGTH: 18
<212> TYPE: DNA
<213> ORGANISM: artificial sequence
<220> FEATURE:
<223> OTHER INFORMATION: antiprobe with 3' acceptor for
      Mycobacterium tuberculosis

<400> SEQUENCE: 23
atgcatcccg tggtccta                                                    18

<210> SEQ ID NO 24
<211> LENGTH: 18
<212> TYPE: DNA
<213> ORGANISM: artificial sequence
<220> FEATURE:
<223> OTHER INFORMATION: avium probe with 3' acceptor for
      for Mycobacterium avium

<400> SEQUENCE: 24
atgcgtcttg aggtccta                                                    18

<210> SEQ ID NO 25
<211> LENGTH: 27
<212> TYPE: DNA
<213> ORGANISM: artificial sequence
<220> FEATURE:
<223> OTHER INFORMATION: 103k probe with 5' donor and 3' block

<400> SEQUENCE: 25
ctgttactga tttttctttt tttaacc                                          27

<210> SEQ ID NO 26
<211> LENGTH: 27
<212> TYPE: DNA
<213> ORGANISM: artificial sequence
<220> FEATURE:
<223> OTHER INFORMATION: 103n probe with 5' donor and 3' block

<400> SEQUENCE: 26
ctgttactga tttgttcttt tttaacc                                          27

<210> SEQ ID NO 27
<211> LENGTH: 22
<212> TYPE: DNA
<213> ORGANISM: artificial sequence
<220> FEATURE:
<223> OTHER INFORMATION: 103k antiprobe with 3' acceptor
```

<400> SEQUENCE: 27
aaaaagaaaa aatcagtaac ag                                              22

<210> SEQ ID NO 28
<211> LENGTH: 22
<212> TYPE: DNA
<213> ORGANISM: artificial sequence
<220> FEATURE:
<223> OTHER INFORMATION: 103n antiprobe with 3' acceptor

<400> SEQUENCE: 28
aaaaagaaca aatcagtaac ag                                              22

<210> SEQ ID NO 29
<211> LENGTH: 42
<212> TYPE: DNA
<213> ORGANISM: artificial sequence
<220> FEATURE:
<223> OTHER INFORMATION: probe with 5' fluorescent label

<400> SEQUENCE: 29
tcaggaaccg ccaatcagcc gatccggctc ggcgtgcatg tc                        42

<210> SEQ ID NO 30
<211> LENGTH: 9
<212> TYPE: DNA
<213> ORGANISM: artificial sequence
<220> FEATURE:
<223> OTHER INFORMATION: antiprobe with 3' quencher

<400> SEQUENCE: 30 ggttcctga                                                              9

<210> SEQ ID NO 31
<211> LENGTH: 36
<212> TYPE: DNA
<213> ORGANISM: artificial sequence
<220> FEATURE:
<223> OTHER INFORMATION: target sequence

<400> SEQUENCE: 31
cggatcggct gattggcggt tcctgacaga acatcg                               36

<210> SEQ ID NO 32
<211> LENGTH: 12
<212> TYPE: DNA
<213> ORGANISM: artificial sequence
<220> FEATURE:
<223> OTHER INFORMATION: antiprobe with 3' quencher

<400> SEQUENCE: 32
gacatgcacg cc                                                         12

<210> SEQ ID NO 33
<211> LENGTH: 32
<212> TYPE: DNA
<213> ORGANISM: artificial sequence
<220> FEATURE:
<223> OTHER INFORMATION: probe with 5' fluorescent label

<400> SEQUENCE: 33
tcaggaaccg ccaatcagcc ggcgtgcatg tc                                   32

```
<210> SEQ ID NO 34
<211> LENGTH: 33
<212> TYPE: DNA
<213> ORGANISM: artificial sequence
<220> FEATURE:
<223> OTHER INFORMATION: probe with 5' fluorescent label

<400> SEQUENCE: 34
gtaccctacc gtgtgtggcc gcgagacact ctt                              33

<210> SEQ ID NO 35
<211> LENGTH: 9
<212> TYPE: DNA
<213> ORGANISM: artificial sequence
<220> FEATURE:
<223> OTHER INFORMATION: antiprobe with 3' quencher

<400> SEQUENCE: 35 gtagggtac                                                          9

<210> SEQ ID NO 36
<211> LENGTH: 31
<212> TYPE: DNA
<213> ORGANISM: artificial sequence
<220> FEATURE:
<223> OTHER INFORMATION: probe with 5' fluorescent label

<400> SEQUENCE: 36
cgtgtggccg cgagacactc ttggcgtgca t                                31

<210> SEQ ID NO 37
<211> LENGTH: 9
<212> TYPE: DNA
<213> ORGANISM: artificial sequence
<220> FEATURE:
<223> OTHER INFORMATION: antiprobe with 3' quencher

<400> SEQUENCE: 37 atgcacgcc                                                          9

<210> SEQ ID NO 38
<211> LENGTH: 43
<212> TYPE: DNA
<213> ORGANISM: artificial sequence
<220> FEATURE:
<223> OTHER INFORMATION: target sequence

<400> SEQUENCE: 38 tttaagagt gtctcgcggcc acacgaaagt agggtaccta tgt                   43

<210> SEQ ID NO 39
<211> LENGTH: 31
<212> TYPE: DNA
<213> ORGANISM: artificial sequence
<220> FEATURE:
<223> OTHER INFORMATION: probe with 5' fluorescent label

<400> SEQUENCE: 39 agcgtccat cccccgactgg gcgtgcatgt c                                31

<210> SEQ ID NO 40
<211> LENGTH: 46
<212> TYPE: DNA
<213> ORGANISM: artificial sequence
<220> FEATURE:
<223> OTHER INFORMATION: probe with 5' fluorescent label
```

```
<400> SEQUENCE: 40 agcgtccat cccccgactgc caggagcaga gatcggcgtg catgtc         46

<210> SEQ ID NO 41
<211> LENGTH: 9
<212> TYPE: DNA
<213> ORGANISM: artificial sequence
<220> FEATURE:
<223> OTHER INFORMATION: antiprobe with 3' quencher

<400> SEQUENCE: 41 atggacgct                                                    9

<210> SEQ ID NO 42
<211> LENGTH: 31
<212> TYPE: DNA
<213> ORGANISM: artificial sequence
<220> FEATURE:
<223> OTHER INFORMATION: probe with 5' fluorescent label

<400> SEQUENCE: 42
tcgaattaat ccacatgctc cgggcgtgca t                          31

<210> SEQ ID NO 43
<211> LENGTH: 9
<212> TYPE: DNA
<213> ORGANISM: artificial sequence
<220> FEATURE:
<223> OTHER INFORMATION: antiprobe with 3' quencher

<400> SEQUENCE: 43 ttaattcga                                                    9

<210> SEQ ID NO 44
<211> LENGTH: 31
<212> TYPE: DNA
<213> ORGANISM: artificial sequence
<220> FEATURE:
<223> OTHER INFORMATION: probe with 5' fluorescent label

<400> SEQUENCE: 44
ttttggcggc ggactgatcg gtggcgtgca t                          31

<210> SEQ ID NO 45
<211> LENGTH: 9
<212> TYPE: DNA
<213> ORGANISM: artificial sequence
<220> FEATURE:
<223> OTHER INFORMATION: antiprobe with 3' quencher

<400> SEQUENCE: 45 ccgccaaaa                                                    9

<210> SEQ ID NO 46
<211> LENGTH: 36
<212> TYPE: DNA
<213> ORGANISM: artificial sequence
<220> FEATURE:
<223> OTHER INFORMATION: target sequence

<400> SEQUENCE: 46
cggatcggct gattggcggt tcctgacaga acatcg                     36
```

```
<210> SEQ ID NO 47
<211> LENGTH: 32
<212> TYPE: DNA
<213> ORGANISM: artificial sequence
<220> FEATURE:
<223> OTHER INFORMATION: probe with 5' fluorescent label

<400> SEQUENCE: 47
ggcgtgcatg tctcaggaac cgccaatcag cc                                    32

<210> SEQ ID NO 48
<211> LENGTH: 42
<212> TYPE: DNA
<213> ORGANISM: artificial sequence
<220> FEATURE:
<223> OTHER INFORMATION: probe with 5' fluorescent label

<400> SEQUENCE: 48
ggcgtgcatg tctcaggaac cgccaatcag ccgatccggc tc                         42

<210> SEQ ID NO 49
<211> LENGTH: 9
<212> TYPE: DNA
<213> ORGANISM: artificial sequence
<220> FEATURE:
<223> OTHER INFORMATION: antiprobe with 3' quencher

<400> SEQUENCE: 49 ggctgatgg                                                               9

<210> SEQ ID NO 50
<211> LENGTH: 9
<212> TYPE: DNA
<213> ORGANISM: artificial sequence
<220> FEATURE:
<223> OTHER INFORMATION: antiprobe with 3' quencher

<400> SEQUENCE: 50 gagccggat                                                               9

<210> SEQ ID NO 51
<211> LENGTH: 12
<212> TYPE: DNA
<213> ORGANISM: artificial sequence
<220> FEATURE:
<223> OTHER INFORMATION: primer

<400> SEQUENCE: 51
gacatgcacg cc                                                          12

<210> SEQ ID NO 52
<211> LENGTH: 22
<212> TYPE: DNA
<213> ORGANISM: artificial sequence
<220> FEATURE:
<223> OTHER INFORMATION: primer/probe with 5' fluorescent label

<400> SEQUENCE: 52
tggcagcctg tgggccagga cg                                               22

<210> SEQ ID NO 53
<211> LENGTH: 22
<212> TYPE: DNA
<213> ORGANISM: artificial sequence
<220> FEATURE:
<223> OTHER INFORMATION: primer/probe with 5' fluorescent label
```

```
<400> SEQUENCE: 53
tggcagcctg tgggccagga cc                                                22

<210> SEQ ID NO 54
<211> LENGTH: 18
<212> TYPE: DNA
<213> ORGANISM: artificial sequence
<220> FEATURE:
<223> OTHER INFORMATION: antiprobe with 3' quencher

<400> SEQUENCE: 54
ctggcccaca ggctgcca                                                     18

<210> SEQ ID NO 55
<211> LENGTH: 21
<212> TYPE: DNA
<213> ORGANISM: artificial sequence
<220> FEATURE:
<223> OTHER INFORMATION: primer

<400> SEQUENCE: 55
tctcgactcc agctgtaggt t                                                 21

<210> SEQ ID NO 56
<211> LENGTH: 30
<212> TYPE: DNA
<213> ORGANISM: artificial sequence
<220> FEATURE:
<223> OTHER INFORMATION: primer/probe with 5' fluorescent label

<400> SEQUENCE: 56
cccccccctg gcagcctgtg ggccaggacc                                        30

<210> SEQ ID NO 57
<211> LENGTH: 34
<212> TYPE: DNA
<213> ORGANISM: artificial sequence
<220> FEATURE:
<223> OTHER INFORMATION: primer/probe with 5' fluorescent label

<400> SEQUENCE: 57
cccccccccc acatccagta ctgttactga ttct                                   34

<210> SEQ ID NO 58
<211> LENGTH: 23
<212> TYPE: DNA
<213> ORGANISM: artificial sequence
<220> FEATURE:
<223> OTHER INFORMATION: primer/probe with 5' fluorescent label

<400> SEQUENCE: 58
aaggccagtc cagccaatga cct                                               23

<210> SEQ ID NO 59
<211> LENGTH: 20
<212> TYPE: DNA
<213> ORGANISM: artificial sequence
<220> FEATURE:
<223> OTHER INFORMATION: antiprobe with 3' quencher

<400> SEQUENCE: 59
tcattggctg gactggcctt                                                   20
```

-continued

<210> SEQ ID NO 60
<211> LENGTH: 30
<212> TYPE: DNA
<213> ORGANISM: artificial sequence
<220> FEATURE:
<223> OTHER INFORMATION: Taqman probe

<400> SEQUENCE: 60
agaaggccag tccagccaat gacctctgtt                                    30

<210> SEQ ID NO 61
<211> LENGTH: 22
<212> TYPE: DNA
<213> ORGANISM: artificial sequence
<220> FEATURE:
<223> OTHER INFORMATION: primer

<400> SEQUENCE: 61
gccggaatgg tcttacatag tg                                            22

<210> SEQ ID NO 62
<211> LENGTH: 22
<212> TYPE: DNA
<213> ORGANISM: artificial sequence
<220> FEATURE:
<223> OTHER INFORMATION: primer

<400> SEQUENCE: 62
gccggaatgg tcttacatag tg                                            22

<210> SEQ ID NO 63
<211> LENGTH: 25
<212> TYPE: DNA
<213> ORGANISM: artificial sequence
<220> FEATURE:
<223> OTHER INFORMATION: primer

<400> SEQUENCE: 63
tcttcatagt cattgaaatc ccctg                                         25

<210> SEQ ID NO 64
<211> LENGTH: 34
<212> TYPE: DNA
<213> ORGANISM: artificial sequence
<220> FEATURE:
<223> OTHER INFORMATION: primer/probe with 5' fluorescent label

<400> SEQUENCE: 64
cccccccccc acatccagta ctgttactga tggg                               34

<210> SEQ ID NO 65
<211> LENGTH: 25
<212> TYPE: DNA
<213> ORGANISM: artificial sequence
<220> FEATURE:
<223> OTHER INFORMATION: primer/probe with 5' fluorescent label

<400> SEQUENCE: 65
ttcatcaatc ctatctaatc ttgca                                         25

<210> SEQ ID NO 66
<211> LENGTH: 18
<212> TYPE: DNA
<213> ORGANISM: artificial sequence
<220> FEATURE:
<223> OTHER INFORMATION: antiprobe with 3' quencher

```
<400> SEQUENCE: 66
ttagatagga ttgatgaa                                                   18

<210> SEQ ID NO 67
<211> LENGTH: 24
<212> TYPE: DNA
<213> ORGANISM: artificial sequence
<220> FEATURE:
<223> OTHER INFORMATION: primer

<400> SEQUENCE: 67
caatgaagaa gaatccagct attc                                            24

<210> SEQ ID NO 68
<211> LENGTH: 33
<212> TYPE: DNA
<213> ORGANISM: artificial sequence
<220> FEATURE:
<223> OTHER INFORMATION: primer/probe with 5' fluorescent
      label

<400> SEQUENCE: 68
cccccccctt catcaatcct atctaatctt gct                                  33

<210> SEQ ID NO 69
<211> LENGTH: 31
<212> TYPE: DNA
<213> ORGANISM: artificial sequence
<220> FEATURE:
<223> OTHER INFORMATION: primer/probe with 5' fluorescent label

<400> SEQUENCE: 69
ccccccccaa tgaagaagaa tccagctatt c                                    31

<210> SEQ ID NO 70
<211> LENGTH: 43
<212> TYPE: DNA
<213> ORGANISM: artificial sequence
<220> FEATURE:
<223> OTHER INFORMATION: linker/primer

<400> SEQUENCE: 70
gctacgtaga ctagacgttc tgccggaatg gtcttacata gtg                       43

<210> SEQ ID NO 71
<211> LENGTH: 22
<212> TYPE: DNA
<213> ORGANISM: artificial sequence
<220> FEATURE:
<223> OTHER INFORMATION: primer

<400> SEQUENCE: 71
ccctgggtaa cagaggtcat tg                                              22

<210> SEQ ID NO 72
<211> LENGTH: 44
<212> TYPE: DNA
<213> ORGANISM: artificial sequence
<220> FEATURE:
<223> OTHER INFORMATION: linker/primer

<400> SEQUENCE: 72
gctacgtaga ctagacgttc gtatgccatt ccacaacata cacc                      44
```

<210> SEQ ID NO 73
<211> LENGTH: 23
<212> TYPE: DNA
<213> ORGANISM: artificial sequence
<220> FEATURE:
<223> OTHER INFORMATION: primer

<400> SEQUENCE: 73
gtcgcaagga ctaatctgtt tga                                          23

<210> SEQ ID NO 74
<211> LENGTH: 46
<212> TYPE: DNA
<213> ORGANISM: artificial sequence
<220> FEATURE:
<223> OTHER INFORMATION: linker/primer

<400> SEQUENCE: 74
gctacgtaga ctagacgttc gaggaaataa gtggagtaaa attgga                 46

<210> SEQ ID NO 75
<211> LENGTH: 20
<212> TYPE: DNA
<213> ORGANISM: artificial sequence
<220> FEATURE:
<223> OTHER INFORMATION: primer

<400> SEQUENCE: 75
ccatgattgc cagtgctagg                                              20

<210> SEQ ID NO 76
<211> LENGTH: 24
<212> TYPE: DNA
<213> ORGANISM: artificial sequence
<220> FEATURE:
<223> OTHER INFORMATION: primer/probe with 5' quencher

<400> SEQUENCE: 76
gtatgccatt ccacaacata cacc                                         24

<210> SEQ ID NO 77
<211> LENGTH: 20
<212> TYPE: DNA
<213> ORGANISM: artificial sequence
<220> FEATURE:
<223> OTHER INFORMATION: antiprobe with 3' fluorescent label

<400> SEQUENCE: 77
tatgttgtgg aatggcatac                                              20

<210> SEQ ID NO 78
<211> LENGTH: 34
<212> TYPE: DNA
<213> ORGANISM: artificial sequence
<220> FEATURE:
<223> OTHER INFORMATION: primer probe with 5' fluorescent label

<400> SEQUENCE: 78
cccccccccc acatccagta ctgttactga ttgg                              34

<210> SEQ ID NO 79
<211> LENGTH: 23
<212> TYPE: DNA
<213> ORGANISM: artificial sequence
<220> FEATURE:
<223> OTHER INFORMATION: primer

```
<400> SEQUENCE: 79
ttgggcctga aaatccatac aat                                          23

<210> SEQ ID NO 80
<211> LENGTH: 26
<212> TYPE: DNA
<213> ORGANISM: artificial sequence
<220> FEATURE:
<223> OTHER INFORMATION: primer/probe with 5' fluorescent label

<400> SEQUENCE: 80
ccacatccag tactgttact gatttg                                       26

<210> SEQ ID NO 81
<211> LENGTH: 18
<212> TYPE: DNA
<213> ORGANISM: artificial sequence
<220> FEATURE:
<223> OTHER INFORMATION: antiprobe with 3' quencher

<400> SEQUENCE: 81
taacagtact ggatgtgg                                                18

<210> SEQ ID NO 82
<211> LENGTH: 22
<212> TYPE: DNA
<213> ORGANISM: artificial sequence
<220> FEATURE:
<223> OTHER INFORMATION: primer

<400> SEQUENCE: 82
tcaagacttc tgggaagttc aa                                           22

<210> SEQ ID NO 83
<211> LENGTH: 34
<212> TYPE: DNA
<213> ORGANISM: artificial sequence
<220> FEATURE:
<223> OTHER INFORMATION: primer/probe with 5' fluorescent label

<400> SEQUENCE: 83
cccccccccc acatccagta ctgttactga tttg                              34

<210> SEQ ID NO 84
<211> LENGTH: 34
<212> TYPE: DNA
<213> ORGANISM: artificial sequence
<220> FEATURE:
<223> OTHER INFORMATION: primer/probe with 5' fluorescent label

<400> SEQUENCE: 84
cccccccccc acatccagta ctgttactga ttgg                              34

<210> SEQ ID NO 85
<211> LENGTH: 20
<212> TYPE: DNA
<213> ORGANISM: artificial sequence
<220> FEATURE:
<223> OTHER INFORMATION: antiprobe with 3' quencher

<400> SEQUENCE: 85
tagtctacgt agcgataggg                                              20
```